(12) United States Patent
Schoenfisch et al.

(10) Patent No.: US 9,201,037 B2
(45) Date of Patent: Dec. 1, 2015

(54) MICROFLUIDIC NITRIC OXIDE SENSOR

(76) Inventors: Mark Schoenfisch, Chapel Hill, NC (US); Benjamin Privett, Siler City, NC (US); John Ramsey, Chapel Hill, NC (US); William Henley, Chapel Hill, NC (US)

( * ) Notice: Subject to any disclaimer, the term of this patent is extended or adjusted under 35 U.S.C. 154(b) by 0 days.

(21) Appl. No.: 14/005,259

(22) PCT Filed: Mar. 14, 2012

(86) PCT No.: PCT/US2012/029076
§ 371 (c)(1),
(2), (4) Date: Sep. 14, 2013

(87) PCT Pub. No.: WO2012/125723
PCT Pub. Date: Sep. 20, 2012

(65) Prior Publication Data
US 2014/0008220 A1      Jan. 9, 2014

Related U.S. Application Data

(60) Provisional application No. 61/452,461, filed on Mar. 14, 2011.

(51) Int. Cl.
*G01N 27/28* (2006.01)
*G01N 27/404* (2006.01)
*G01N 33/49* (2006.01)
*B01L 3/00* (2006.01)

(52) U.S. Cl.
CPC ............ *G01N 27/28* (2013.01); *G01N 27/4045* (2013.01); *G01N 33/4915* (2013.01); *B01L 3/5027* (2013.01); *Y10T 29/49117* (2015.01)

(58) Field of Classification Search
CPC .............. G01N 27/28; G01N 27/4045; G01N 33/4915; B01L 3/5027
USPC .................................. 204/412, 431, 432, 271
See application file for complete search history.

(56) References Cited

U.S. PATENT DOCUMENTS

| | | |
|---|---|---|
| 2003/0150725 A1* | 8/2003 | Tschuncky .................... 204/415 |
| 2007/0023296 A1* | 2/2007 | Cai et al. ........................ 205/782 |
| 2007/0045128 A1 | 3/2007 | Krafthefer |
| 2009/0288960 A1 | 11/2009 | Rubin |
| 2010/0051480 A1* | 3/2010 | Schoenfisch et al. ......... 205/781 |

OTHER PUBLICATIONS

Written Opinion of the International Searching Authority for PCT/US20121029076 mailed Oct. 30, 2012.
International Preliminary Report on Patentability for PCT/US2012/029076 issued Sep. 17, 2013.

(Continued)

*Primary Examiner* — J. Christopher Ball
(74) *Attorney, Agent, or Firm* — Ben Schroeder Law PLLC

(57) ABSTRACT

The presently disclosed subject matter relates to a microfluidic device for measuring an amount of a molecular species in a sample. The device comprises a body and an electrode assembly, the electrode assembly comprising at least one electrode coupled to the body. The device also includes a gas permeable membrane disposed on at least one electrode and a detector for measuring a current at each of the electrodes. Further, the device comprises a channel defined between a substantially planar substrate and planar cover glass. The presently disclosed subject matter also relates to methods of making the microfluidic device.

21 Claims, 24 Drawing Sheets

(56) References Cited

OTHER PUBLICATIONS

International Search Report for PCT/US2012/029076 mailed Oct. 30, 2012.

Prosecution history of PCT/US2012/029076 filed Mar. 14, 2012.
Zhang, X., Frontiers in Bioscience, 9, (2004), pp. 3434-3446.
U.S. Appl. No. 61/452,444, entitled Photolytic Cleavage and Detection of S-Nitrosothiols.

* cited by examiner

US 9,201,037 B2

MICROFLUIDIC NITRIC OXIDE SENSOR

This application claims priority under 35 USC 371 to PCT/US2012/029076 filed Mar. 14, 2012, which in turn claims priority under 35 USC 119 to U.S. Provisional Application No. 61/452,461 filed Mar. 14, 2011, both of which are hereby incorporated by reference in their entireties.

This invention was made with government support under Grant No. EB000708 awarded by the National Institutes of Health. The government has certain rights in the invention.

FIELD OF THE INVENTION

Embodiments of the present invention relate to microfluidic devices for measuring molecular species, such as nitric oxide, nitrosothiols, and/or nitrates in fluids.

BACKGROUND OF THE INVENTION

Nitric oxide (NO) is a diatomic free radical endogenously synthesized in the human body when L-arginine is converted to L-citrulline by a class of enzymes known nitric oxide synthases (NOS's). Since the first reports describing NO's action as an endothelium-derived relaxation factor, much research has been devoted to elucidating the pathways of NO generation and action in biological milieu. In particular, NO is involved in angiogenesis, wound healing, platelet activation, neurotransmission, vasodilation, immune responses, the inhibition of platelet aggregation, and in blood pressure control. See Zhang, X., *Frontiers in Bioscience*, 9, 3434-3446 (2004).

Sepsis is the $10^{th}$ leading cause of death in the United States, and the leading cause of death in non-cardiac intensive care units (ICUs). Sepsis often originates from medical device infections, and severe cases account for 1 in 5 admissions to ICUs in the U.S. Furthermore, the onset of sepsis corresponds with increased levels of NO. Accordingly, motivation exists to improve the ability to detect the onset of sepsis by increasing speed, accuracy, and ease of diagnosis by NO detection devices and methods.

The detection of NO in blood may be used as a biomarker for sepsis, to evaluate wound healing by measuring NO in wound fluid, and to evaluate the efficacy and NO-release kinetics of pharmaceuticals that directly release, or modulate the endogenous release of NO. Challenges of in vivo biological NO detection may include biofouling (i.e., platelet/protein adhesion and clot formation), noise, and risk of infection. With regard to ex vivo detection of biological NO, challenges for such detection may include the transport of fluids, the reactivity of NO, fluid volume demands, and sensor drift.

Methods for measuring NO directly include chemiluminescence, electron paramagnetic resonance, spectroscopy, and electrochemistry. Measurement of NO with chemiluminescene and electron paramagnetic resonance may provide for more sensitive and direct measurements, but these methods are expensive and require extensive training for accurately measuring NO. Further, these methods for measuring NO are difficult when measuring NO in certain mediums, such as whole blood.

Miniaturized electrochemical sensors represent promising devices for determining the spatial and temporal distribution of NO in physiology, as they are readily miniaturized. Such electrochemical sensors, however, have a number of limitations and challenges that must be addressed, such as low sensitivity, comparatively slow response time, and/or interferences from other readily oxidizable biological species (e.g., nitrate, ascorbic acid, uric acid, dopamine, etc.). Furthermore, such electrochemical sensors require sample sizes greater than tens of milliliters for determining an amount of NO.

Accordingly, there is a need in the art for microfluidic sensors for measuring and detecting molecular species in smaller sample sizes, such as tens of microliters. Further, there is a need for microfluidic sensors that are highly selective for molecular species over other biologically relevant interfering species.

SUMMARY OF THE INVENTION

Embodiments of the present invention are directed to a microfluidic device for measuring an amount of a molecular species in a sample. In one embodiment, the device includes a body and an electrode assembly, the electrode assembly comprising at least one electrode coupled to the body. The device also may include a gas permeable membrane disposed on at least one electrode. Further, in one embodiment of the present invention, the device may include a detector for measuring a current at each of the electrodes.

According to one embodiment, the gas permeable membrane may comprise a polysiloxane network wherein one or more silicon atoms in the polysiloxane network is covalently attached to an alkyl group and one or more silicon atoms in the polysiloxane network is covalently attached to a fluorinated alkyl group. Another embodiment of the present invention may include a gas permeable membrane comprising a mixture of about 1% to 99% by volume fluorosilane. In some embodiments, the silane mixture comprises about 1% to 50% fluorosilane. Another embodiment of the present invention may include a gas permeable membrane comprising a mixture of about 80% by volume methyltrimethoxysilane and 20% by volume (heptadecafluoro-1,1,2,2-tetrahydrodecyl)trimethoxysilane.

According to aspects of the invention, the molecular species in a sample may be selected from the group consisting of nitric oxide, nitrite, and s-nitrosothiols. In one embodiment of the invention, the molecular species may be a gaseous species, such as nitric oxide. In another embodiment, the molecular species may be an aqueous species, such as nitrites or s-nitrosothiols. Further, the sample may comprise a volume of about 1 to 100 µL. In other embodiments, the substantially planar body may comprise a planar substrate and a planar cover glass. The planar substrate may further comprise a reference electrode, and the planar cover glass may further comprise at least one electrode. In another embodiment, the planar cover glass may comprise a working electrode and a counter electrode. The working electrode may be selected from the group of platinum, platinized platinum, tungsten, gold, carbon, carbon fiber, and combinations thereof. The counter electrode may comprise platinum. Further, the reference electrode may comprise silver/silver chloride. In another embodiment of the present invention, the planar cover glass may comprise a plurality of working electrodes, the working electrodes being selected from the group consisting of platinum, platinized platinum, tungsten, gold, carbon, carbon fiber, and combinations thereof. In another embodiment, the planar cover glass may comprise at least one of a reference electrode and/or a counter electrode.

One embodiment of the present invention may include a substantially planar body comprising a planar substrate and a planar cover glass coupled to the substrate. Further, the planar body may include a channel comprising a proximal and distal end, wherein the channel is defined between the planar substrate and the planar body, is in fluid communication with an inlet aperture and an outlet aperture, and is configured to receive at least a portion of the sample therein. According to one embodiment, the inlet aperture is defined in the planar cover glass, and the outlet aperture is defined in the planar cover glass. Further, the planar body may also comprise an insulating material cooperating with the planar substrate and the planar cover glass to define the channel. The inlet aperture may be configured to receive the sample for measuring an amount of a molecular species, and the outlet aperture may be configured to remove the sample from the channel after the microfluidic device has measured the amount of molecular species within the sample. In one embodiment of the present invention, the planar substrate may comprise a material selected from the group consisting of glass, paper, cellulose, fabric, and polymers, such as polydimethylsiloxane, polyimide, polystyrene.

In another embodiment of the present invention, the integrated electrode assembly comprises at least one integrated electrode, wherein the at least one integrated electrode may further comprise a sensor width and a sensor pitch. According to one embodiment, the sensor width may be about 50 to 1000 μm. The sensor pitch may be about 50 to 2500 μm. In one embodiment, the microfluidic device may include a channel having a channel width of about 3 mm and a channel height of about 40 μm. In another embodiment, the channel may have a channel width of about 0.5 mm to 5 mm. One embodiment may include a channel having a channel height of about 20 to 100 microns.

Another aspect of the present invention may include a method of making a microfluidic device for measuring an amount of a molecular species in a sample. The method may include attaching the plurality of electrodes to a substantially planar body, depositing a gas permeable membrane on at least one of the plurality of electrodes, and coupling a detector for measuring current to at least one of the plurality of electrodes. Further, the method may include depositing a gas permeable membrane comprising a polysiloxane network, wherein one or more silicon atoms in the polysiloxane network is covalently attached to an alkyl group and one or more silicon atoms in the polysiloxane network is covalently attached to a fluorinated alkyl group. According to another embodiment of the invention, the method may include providing a gas permeable membrane which comprises a mixture of about 80% by volume methyltrimethoxysilane and 20% by volume (heptadecafluoro-1,1,2,2-tetrahydrodecyl)trimethoxysilane.

According to another embodiment, the plurality of electrodes further comprises an integrated working electrode, an integrated reference electrode, and an integrated counter electrode. Another aspect of the present invention may include preparing the plurality of electrodes prior to coating the electrode with a gas permeable membrane to increase adhesion of the gas permeable membrane to the electrode. The method includes, according to one embodiment, coupling the substrate to a cover glass so as to define a channel for receiving at least a portion of the sample therein and applying an insulating material to the substrate such that the substrate, cover glass, and insulating material cooperate to define the channel. Another embodiment of the invention provides a method for applying a photoresist material to the body.

Another embodiment of the present invention may include a microfluidic device for measuring an amount of a molecular species in a sample which comprises a body comprising a substrate and a cover glass coupled to one another, wherein a channel is defined between the substrate and the cover glass for receiving at least a portion of the sample therein, an electrode assembly comprising at least one electrode coupled to the body, a gas permeable membrane disposed on the at least one electrode, and a detector for measuring current at each of the electrodes so as to determine the amount of a molecular species in the sample. According to one embodiment, a microfluidic device for measuring an amount of a molecular species in a sample may comprise a body comprising a channel for receiving a sample having a volume of less than about 100 μL therein, an electrode assembly comprising at least one electrode coupled to the body, a gas permeable membrane disposed on the at least one electrode, and a detector for measuring current at each of the electrodes so as to determine the amount of a molecular species in the sample.

BRIEF DESCRIPTION OF THE SEVERAL VIEWS OF THE DRAWING(S)

Having thus described the invention in general terms, reference will now be made to the accompanying drawings, which are not necessarily drawn to scale. The drawings are exemplary only, and should not be construed as limiting the invention.

Figure 11:
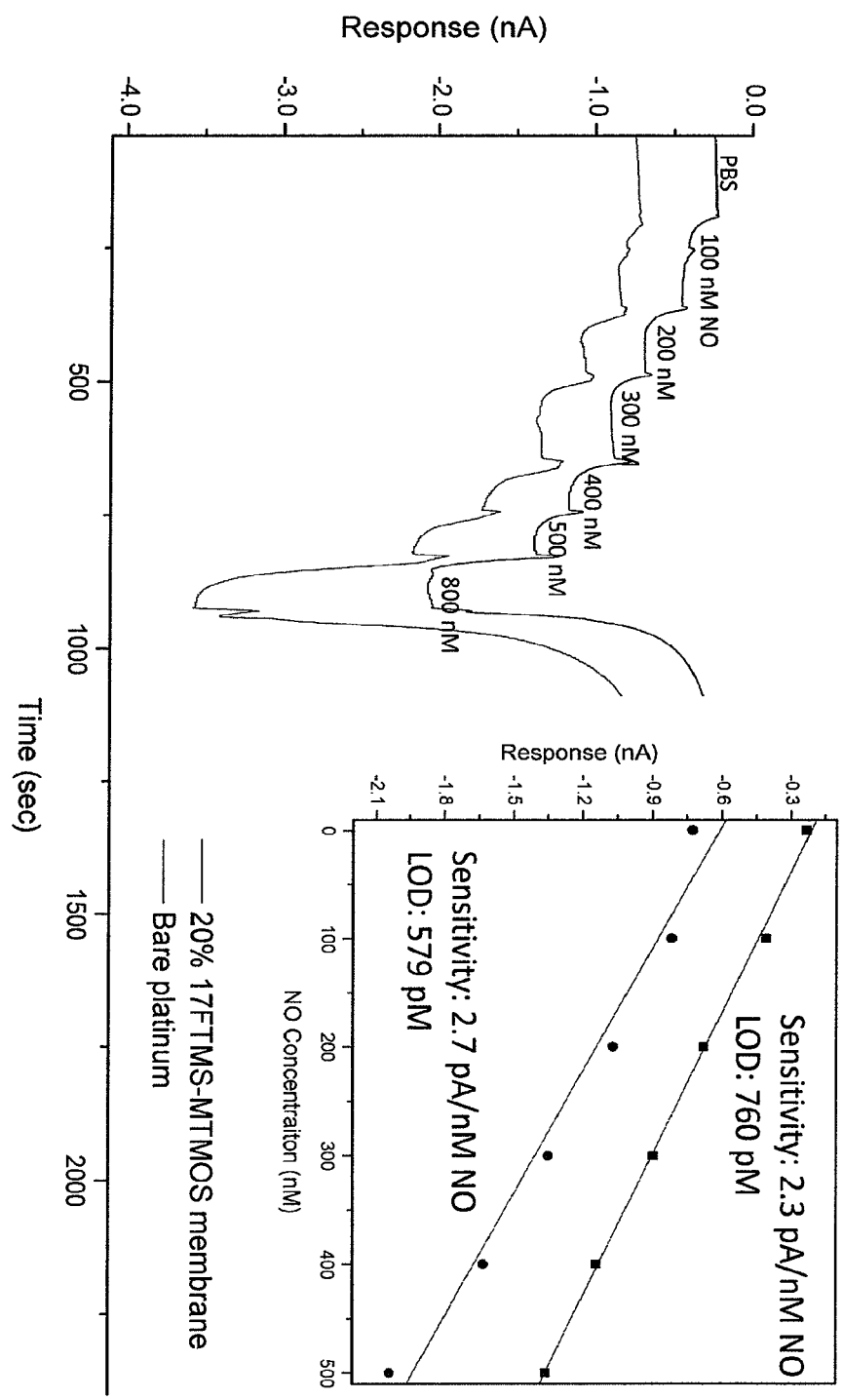
Figure 12:
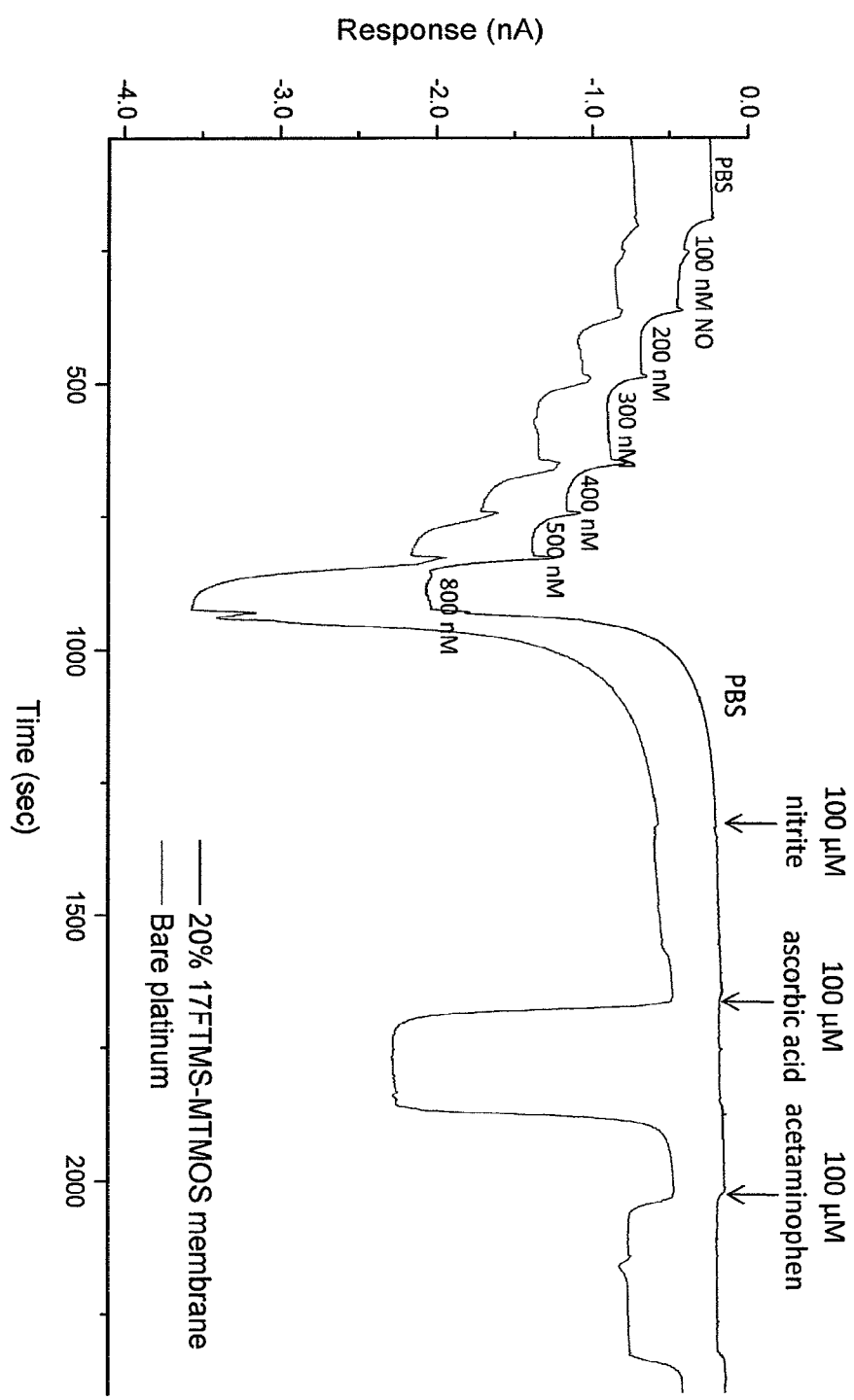
Figure 13:
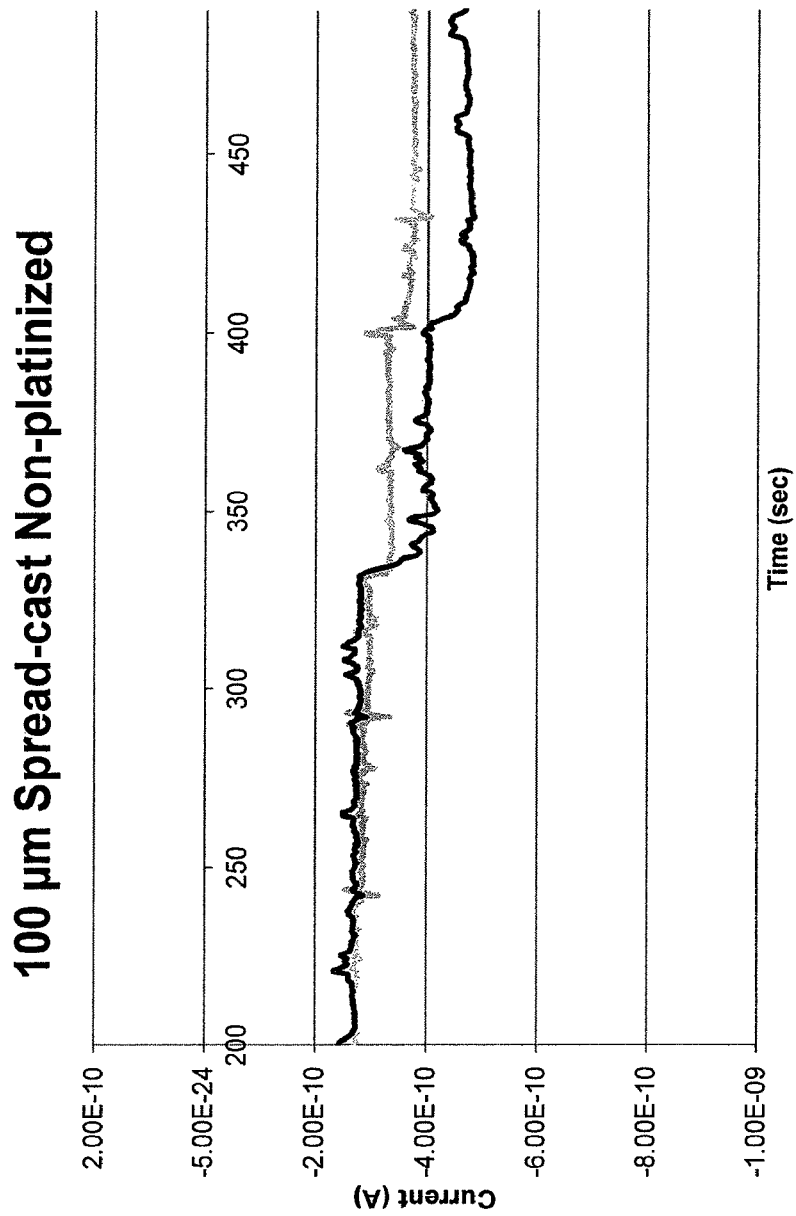
Figure 14:
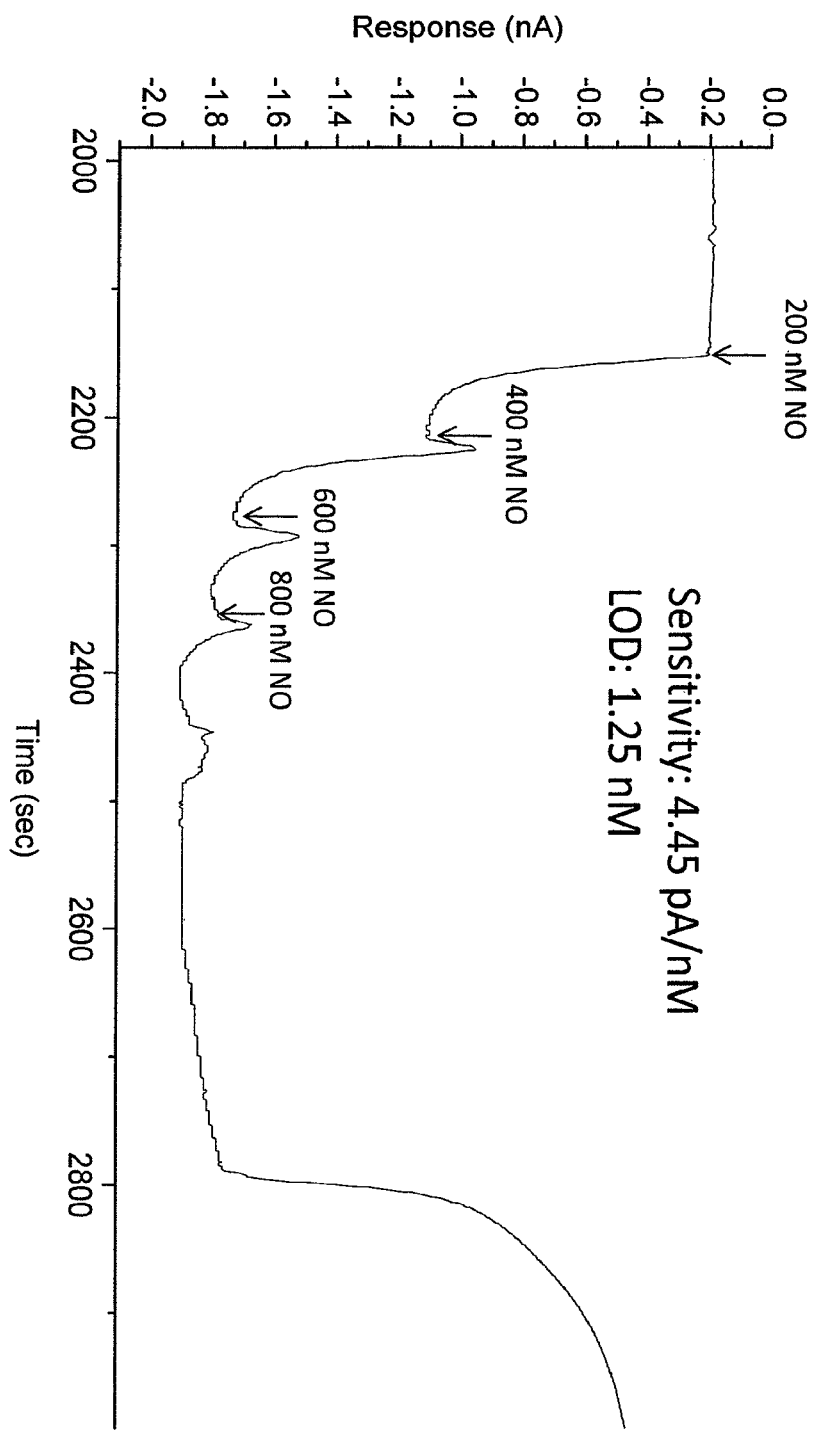
Figure 15:
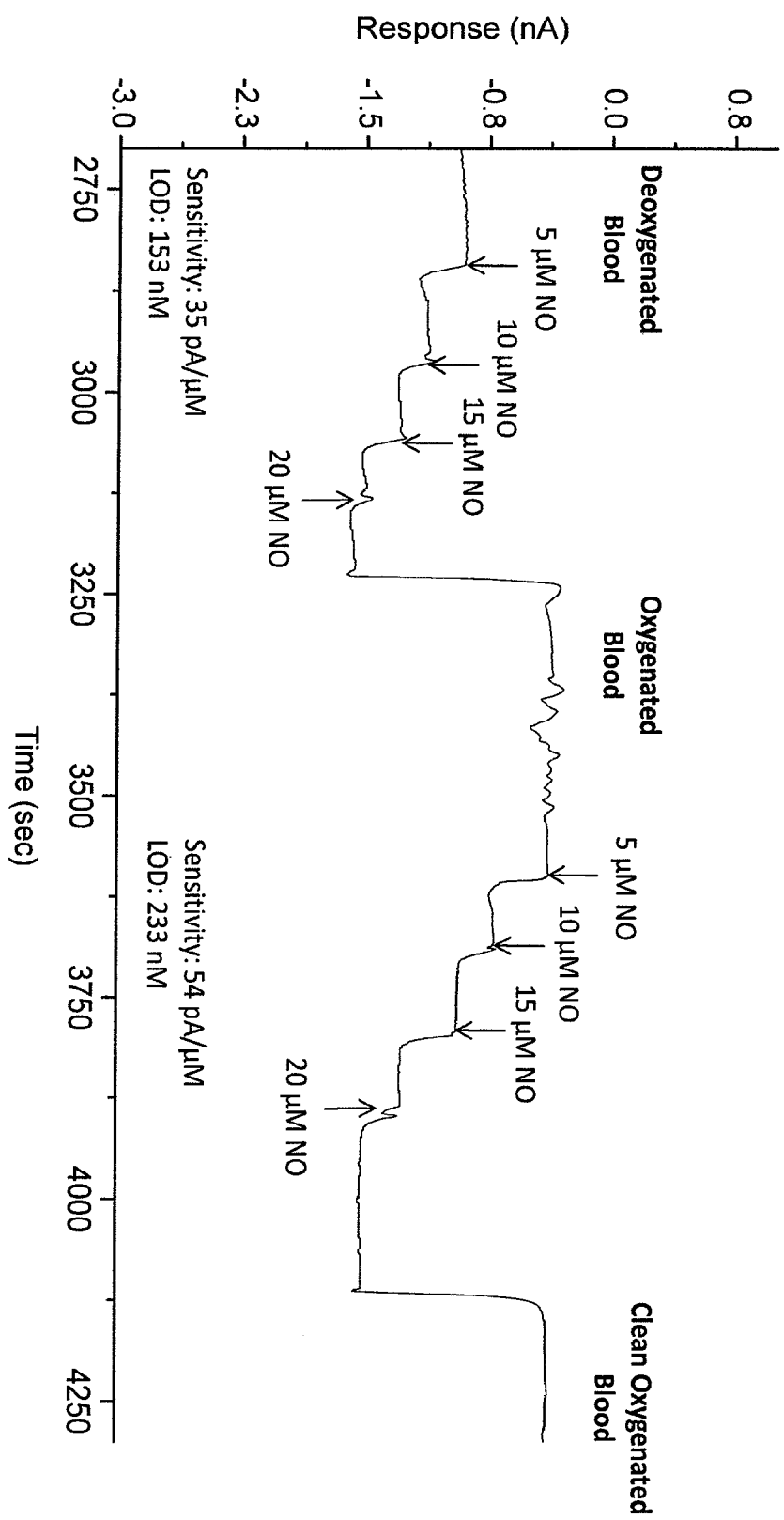
Figure 16:
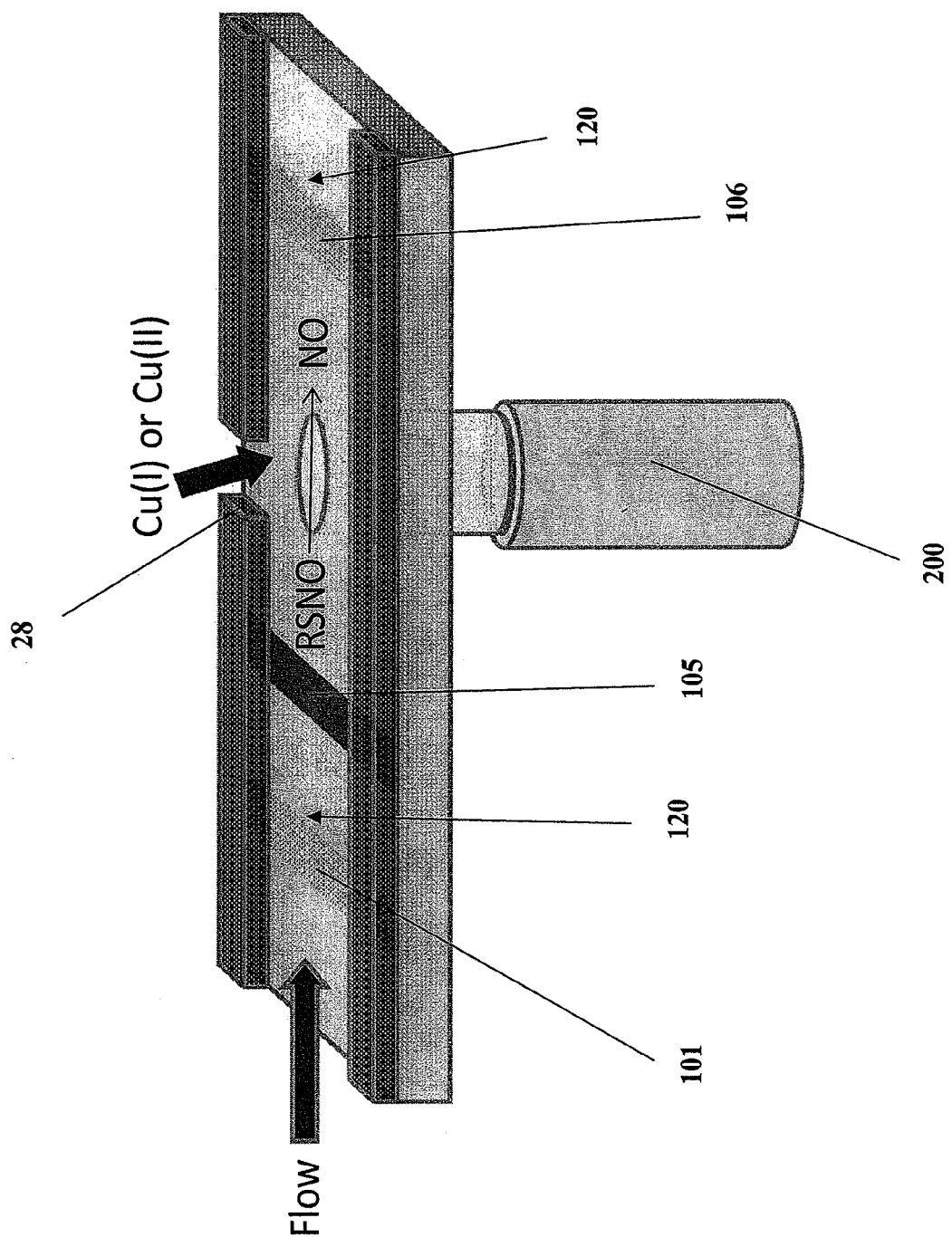
Figure 17A:
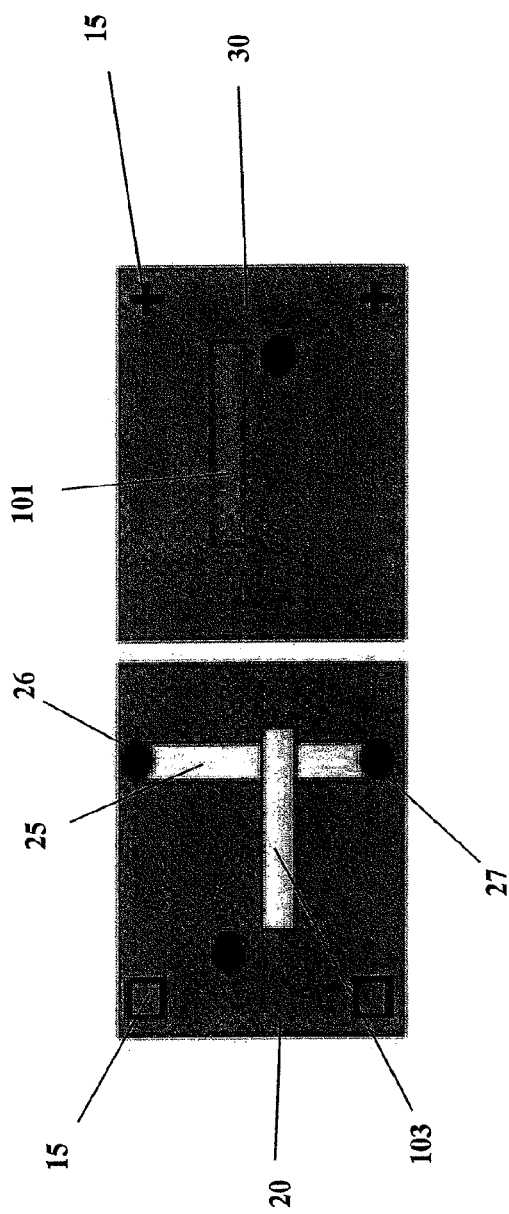
Figure 17B:
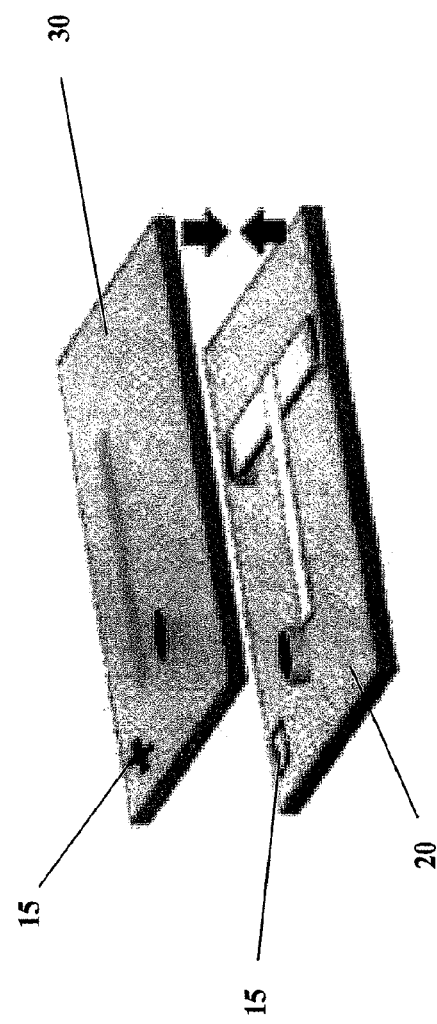
Figure 18:
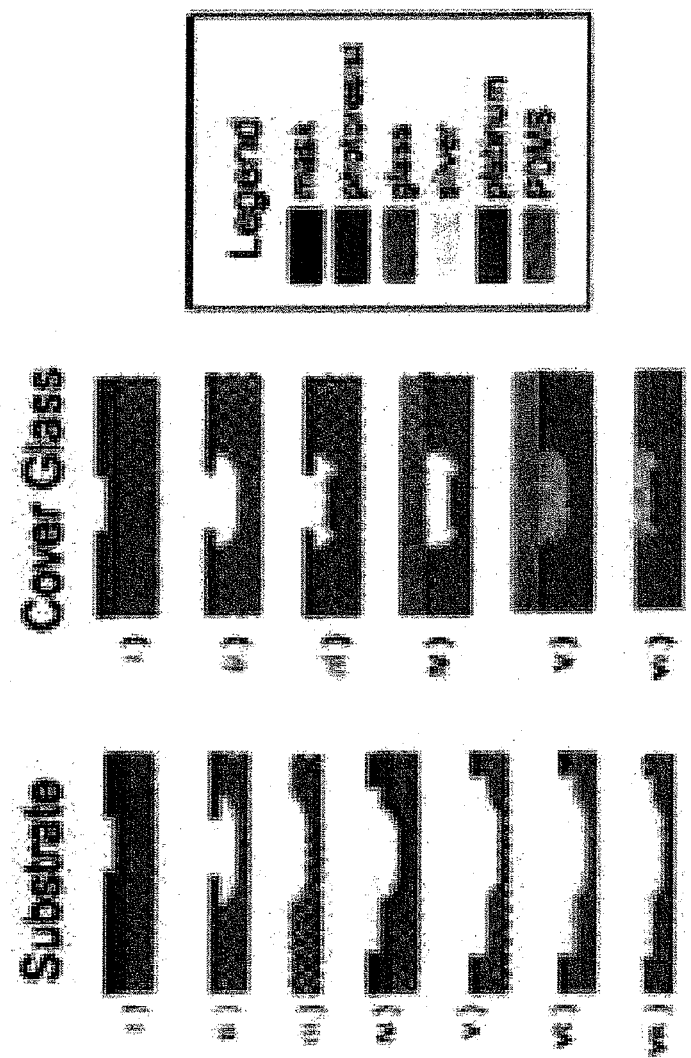
Figure 19:
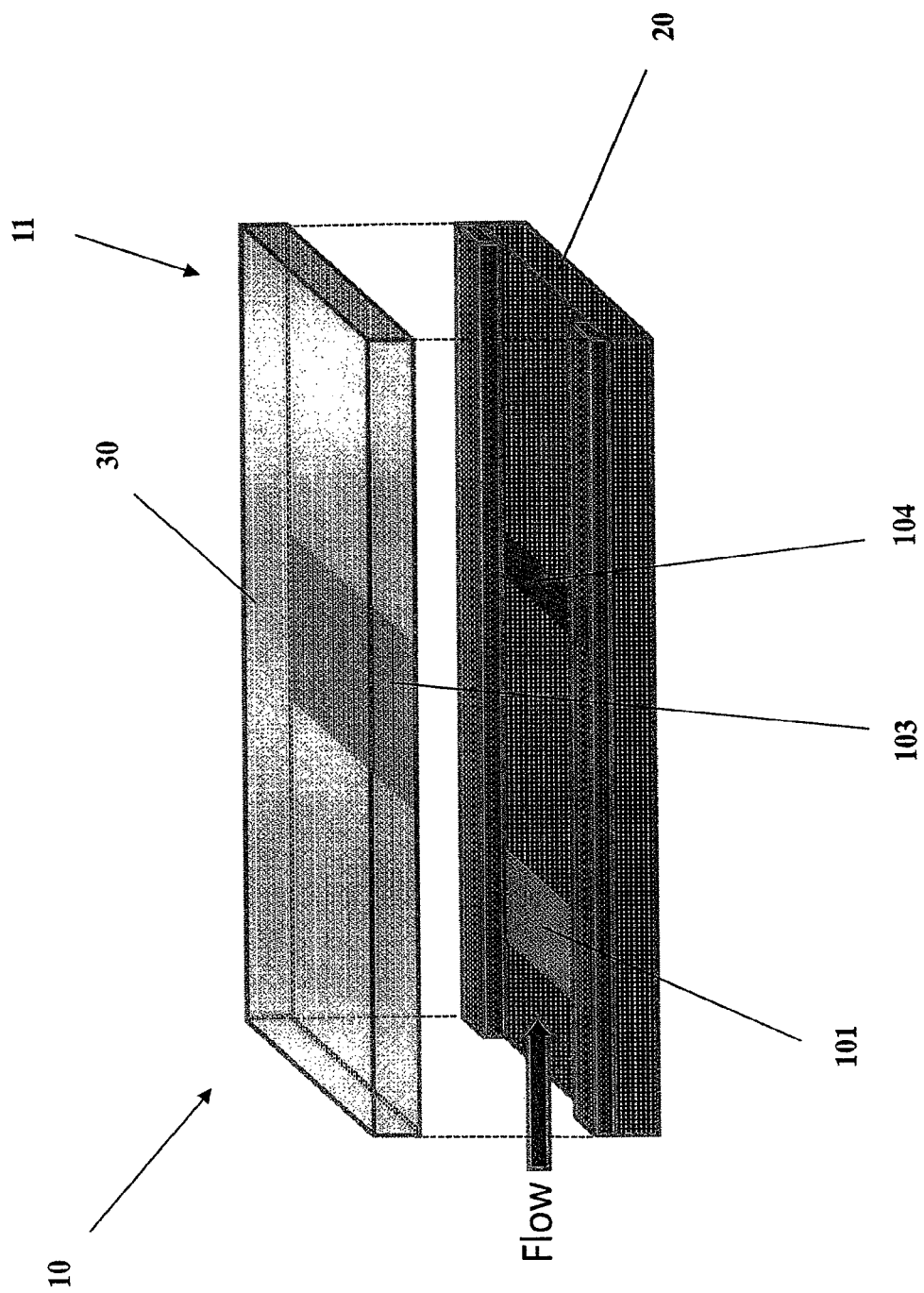
Figure 20:
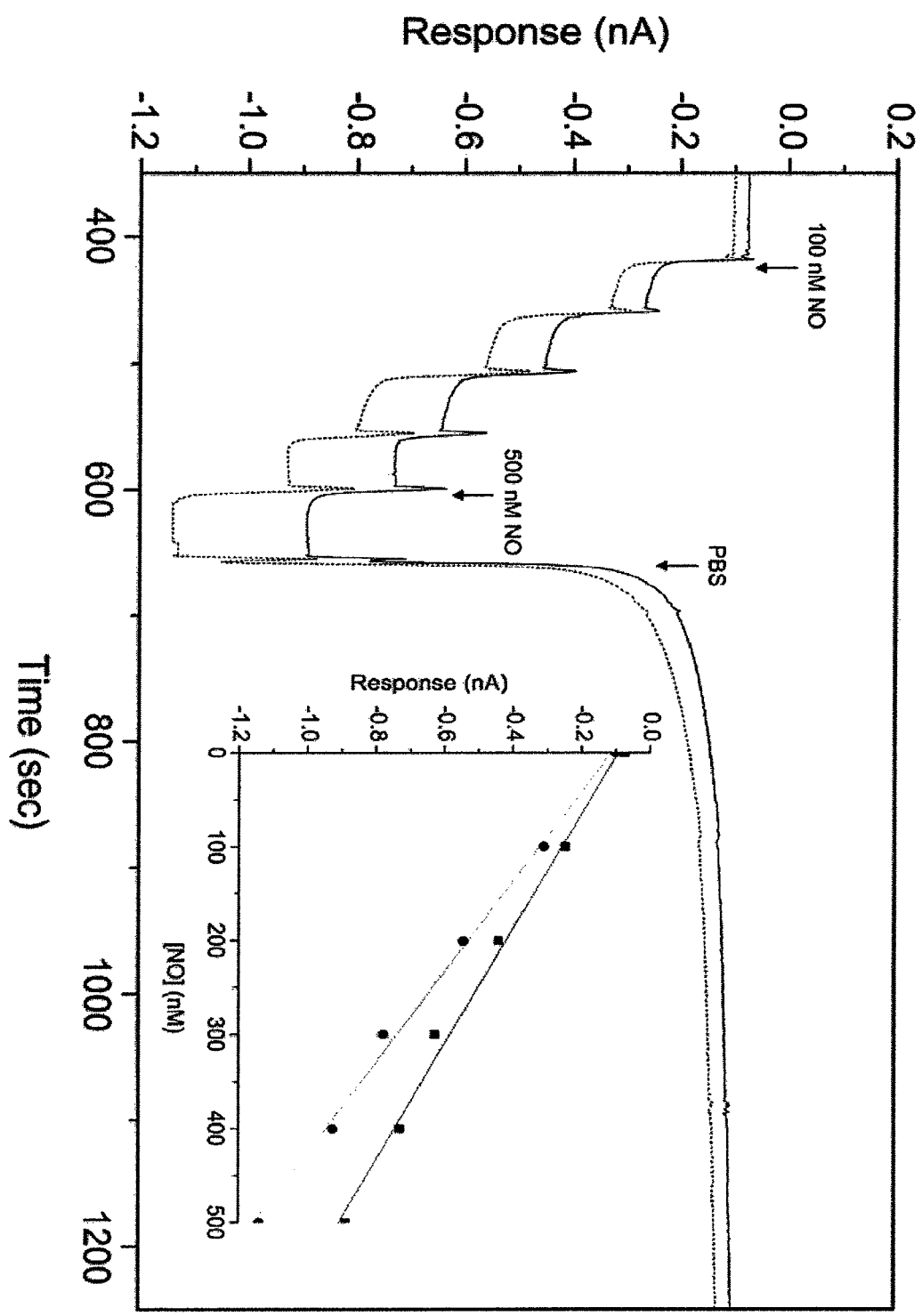
Figure 21:
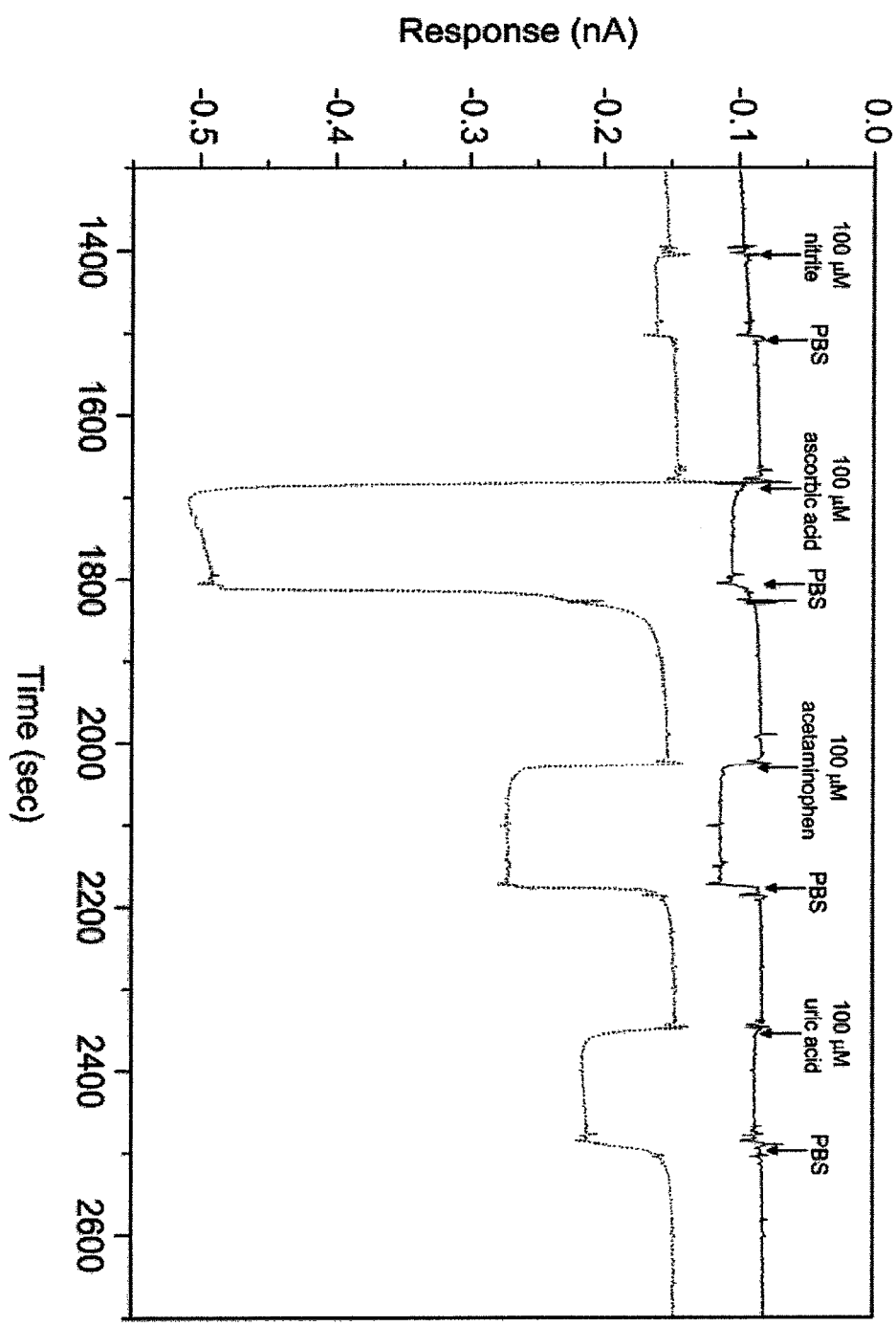
Figure 22:
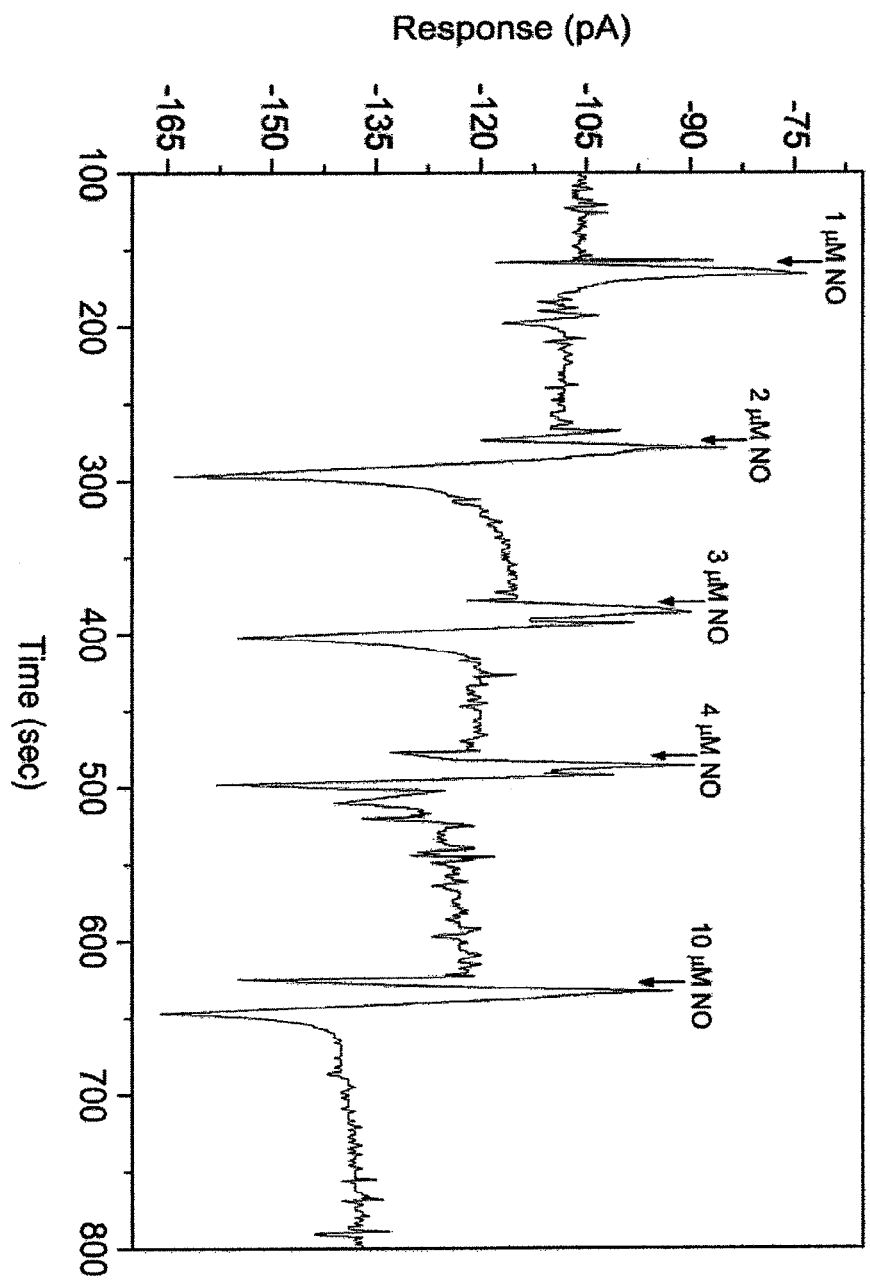
Figure 23:
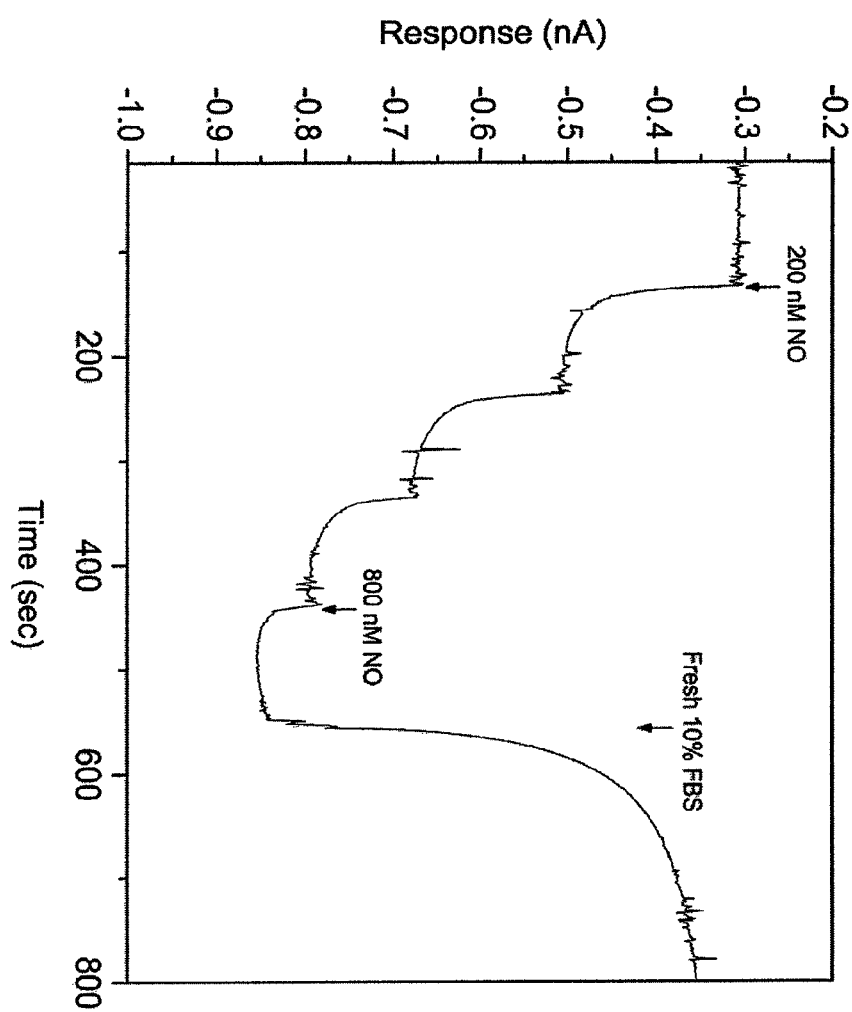
Figure 24:
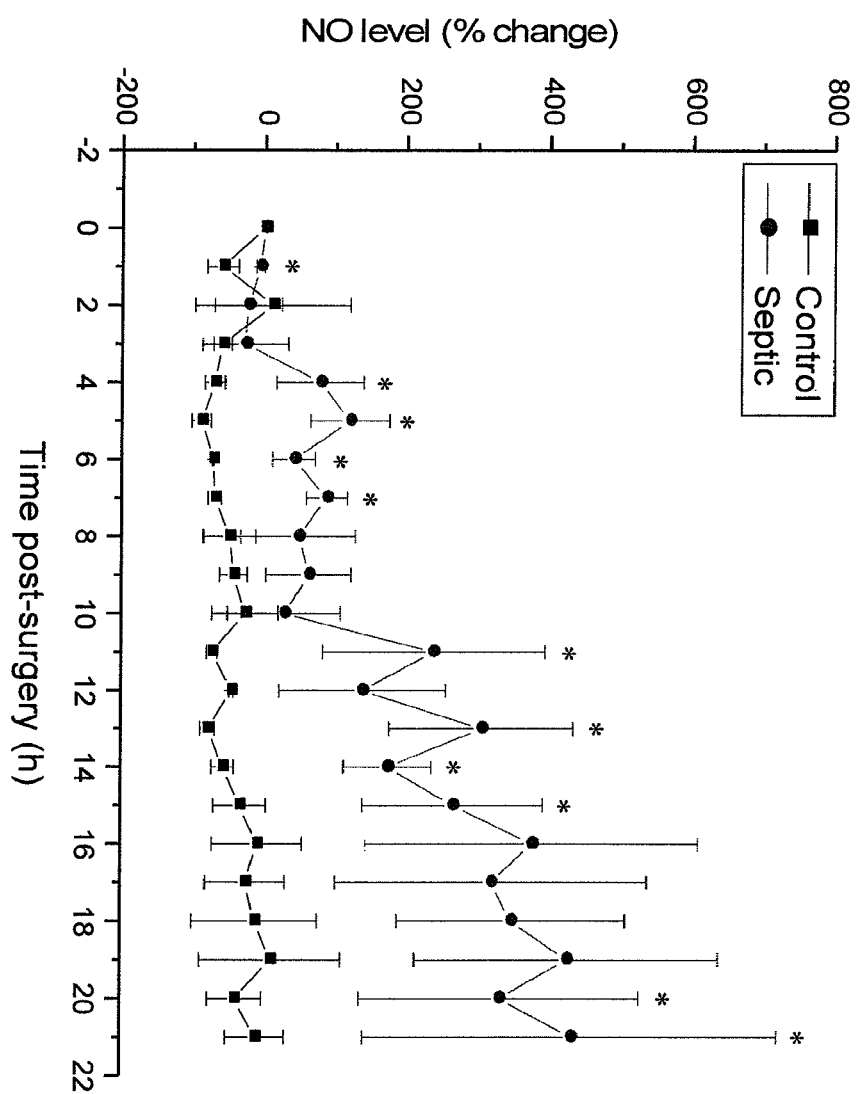

FIG. 11 is a graph illustrating the dynamic response of an electrode coated with a gas permeable membrane and a bare platinum electrode, sensitivity of an electrode coated with a gas permeable membrane and a bare platinum electrode and the limit of detection for an electrode coated with a gas permeable membrane and a bare platinum electrode at nitric oxide concentrations between 100 nM and 800 nM according to one embodiment of the present invention;

FIG. 12 is a graph illustrating the dynamic response of an electrode coated with a gas permeable membrane and a bare platinum membrane at nitric oxide concentrations between 100 nM and 800 nM, and the dynamic response of an electrode coated with a gas permeable membrane and a bare platinum membrane to interferents such as nitrite, ascorbic acid, and acetaminophen at concentrations of 100 nM according to one embodiment of the present invention;

FIG. 13 is a graph of the dynamic response of a non-platinized electrode having a sensor width of 100 μm, the electrode being covered with a gas permeable membrane, which is applied to the electrode by a spread-cast method according to one embodiment of the present invention;

FIG. 14 is a graph illustrating the dynamic response of the microfluidic device to simulated wound fluid, such as 10% fetal bovine serum, having NO concentrations between 200 nM and 800 nM according to one embodiment of the present invention;

FIG. 15 is a graph illustrating the dynamic response of the microfluidic device to deoxygenated and oxygenated whole blood having NO concentrations between 5 μM and 20 μM according to one embodiment of the present invention; and FIG. 16 is a partial view of the microfluidic device according to another embodiment;

FIG. 17a is a top view of a planar substrate and a planar cover glass of the microfluidic device according to one embodiment of the present invention;

FIG. 17b is an exploded perspective view of the microfluidic device according to one embodiment of the present invention;

FIG. 18 is a schematic illustrating a fabrication process of a microfluidic device according to various embodiments of the present invention;

FIG. 19 illustrates a partially exploded view of a portion of a microfluidic device according to one embodiment of the present invention;

FIG. 20 is a graph illustrating the dynamic response of an electrode coated with a gas permeable membrane and a bare platinum electrode to nitric oxide in a phosphate buffered solution flowing at approximately 15 μL/min according to one embodiment of the present invention;

FIG. 21 is a graph illustrating the dynamic response of an electrode coated with a gas permeable membrane and a bare platinum membrane to interferents such as nitrite, ascorbic acid, acetaminophen, and uric acid at concentrations of 100 μM according to one embodiment of the present invention;

FIG. 22 is a graph illustrating the dynamic response of a microfluidic device according to one embodiment of the present invention in response to 1 μM increases of nitric oxide concentrations in whole blood;

FIG. 23 is a graph illustrating the dynamic response of a microfluidic device according to one embodiment of the present invention in response to 200 nM increases of nitric oxide concentrations in a simulated wound fluid; and FIG. 24 is a graph illustrating the dynamic response of a microfluidic device in response to increases in NO levels corresponding to sepsis in porcine models according to one embodiment of the present invention.

DETAILED DESCRIPTION OF THE INVENTION

The present invention now will be described more fully hereinafter with reference to the accompanying drawings, in which some, but not all embodiments of the invention are shown. Indeed these inventions may be embodied in many different forms and should not be construed as limited to the embodiments set forth herein; rather, these embodiments are provided so that this disclosure will satisfy applicable legal requirements. Like numbers refer to like elements throughout.

Embodiments of the present invention may provide improvements over the prior art by, among other things, providing a microfluidic device or sensor for measuring an amount of a molecular species in a sample, such as a gaseous and/or an aqueous species. For example, the microfluidic device may be useful in detecting or measuring NO in blood, which may be used as a biomarker for sepsis. The microfluidic device may also be useful in other biomedical uses, such as point-of-care monitoring of NO levels in blood for disease diagnosis and in wound fluids to prognose wound healing in wounds, such as diabetic foot ulcers. Other embodiments may be useful in measuring NO released from cells, tissues, or biological fluids, such as blood, wound fluid, and urine. Another embodiment may be able to measure NO released from small molecules, polymers, particles, or other micro- and macromolecular scaffolds. Further, embodiments of the present invention may be useful in measuring NO released from environmental or treated waters, bacteria, and fungi.

One advantageous aspect of the present invention may include a microfluidic device for measuring an amount of molecular species in smaller sample sizes. One embodiment may provide a microfluidic device for measuring an amount of molecular species in a sample between 1 μL and 1000 μL. In some embodiments, a microfluidic device may be configured to measure an amount of molecular species in a sample between 1 μL and 400 μL. Another embodiment may provide a microfluidic device for measuring an amount of molecular species in a sample between 1 μL and 100 μL. Accordingly, a microfluidic device according to one embodiment of the present invention may measure an amount of molecular species in a sample without the additional need to stir, homogenize or otherwise prepare the sample. Further, one embodiment may provide a microfluidic device configured to measure or detect an amount of molecular species in a sample in real-time, such as while the sample is flowing through the device.

Figure 1:
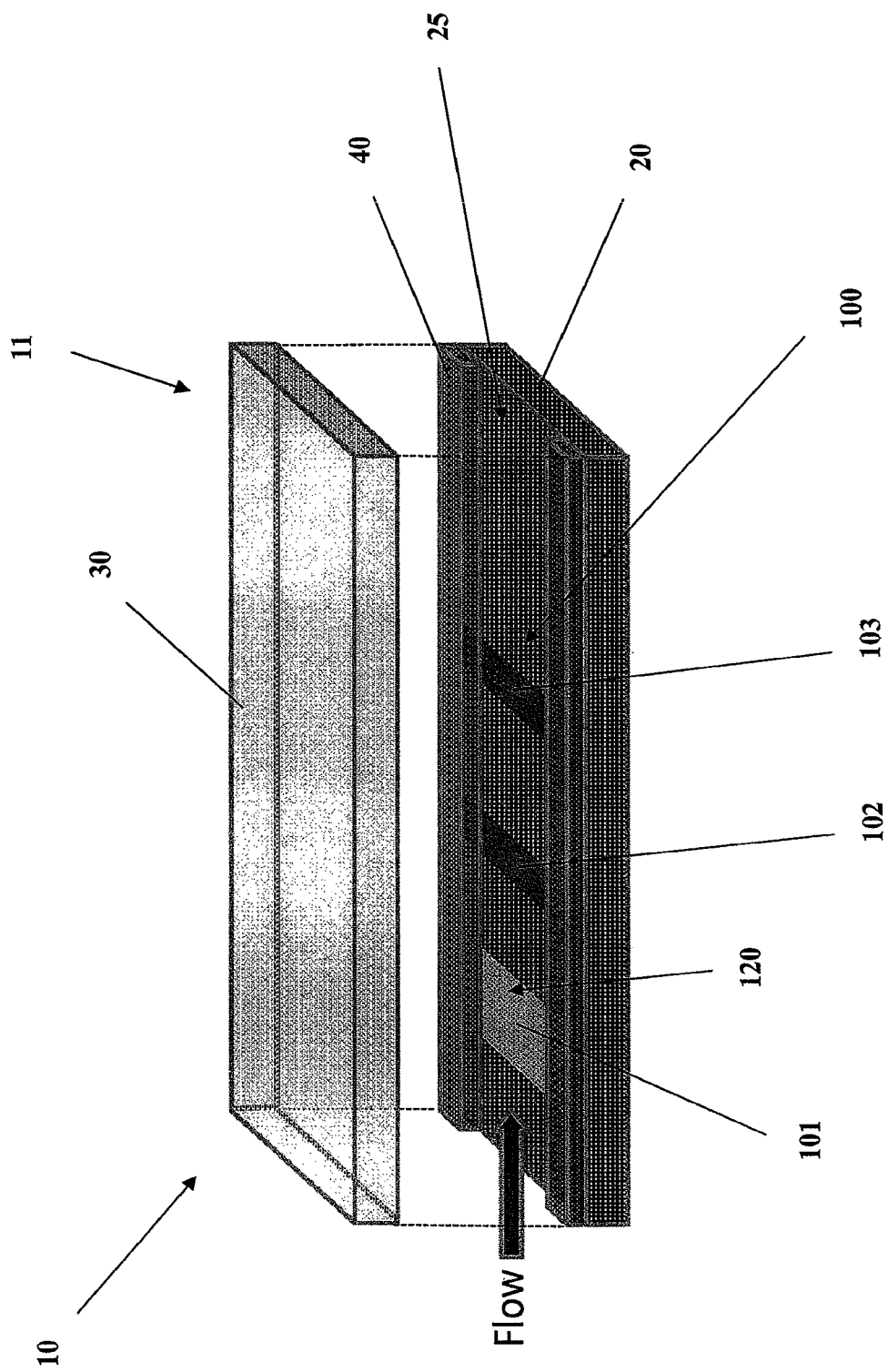
FIG. 1 illustrates a partially exploded view of a portion of a microfluidic device according to one embodiment of the present invention.
Figure 2:
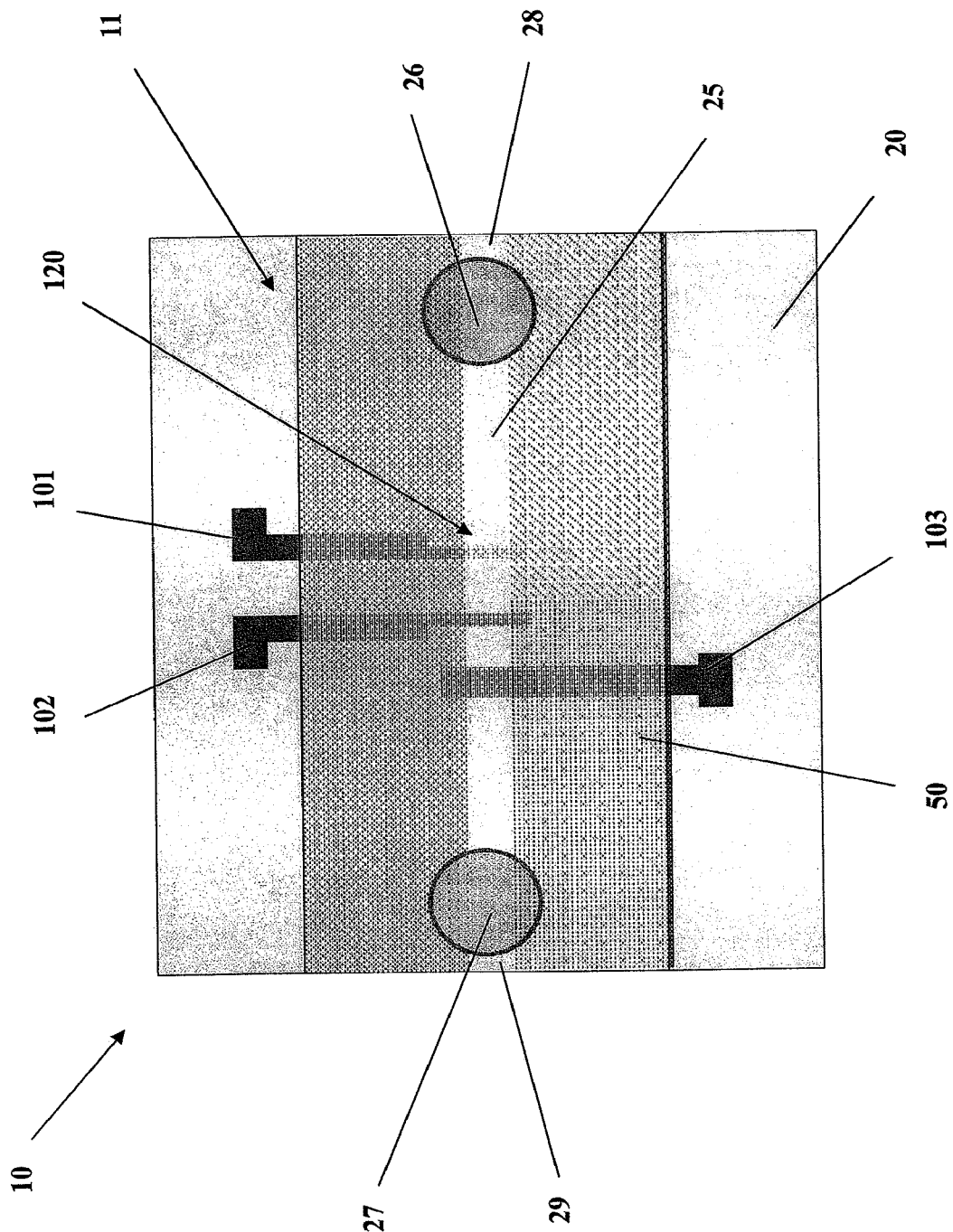
FIG. 2 illustrates a top view of the microfluidic device according to one embodiment of the present invention.
Figure 3:
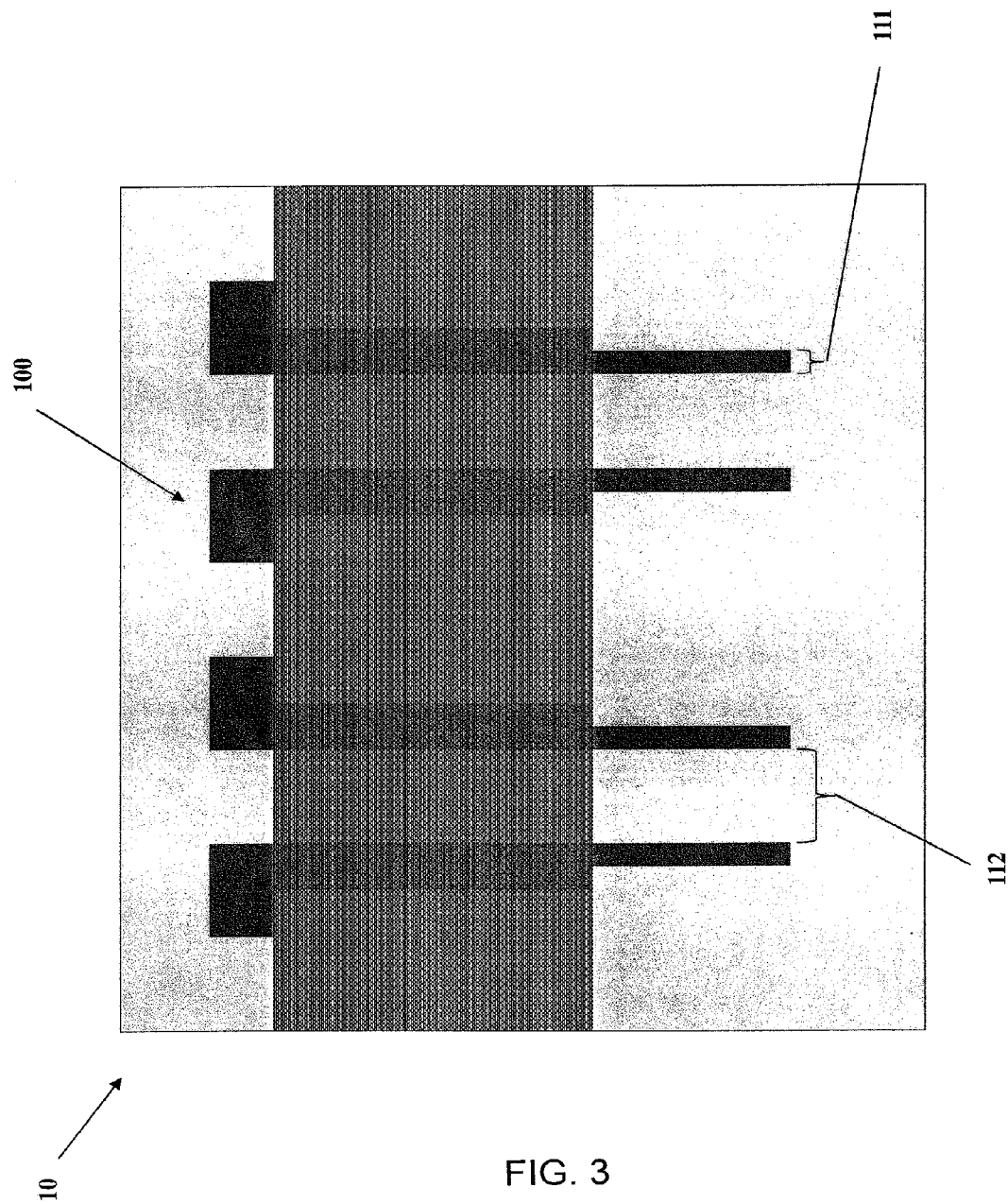
FIG. 3 illustrates a top view of a portion of the microfluidic device according to one embodiment of the present invention.

In one embodiment, FIGS. 1-3 illustrates that a microfluidic device 10, which may be referred to generally as a sensor, includes a body 11 and an electrode assembly 100. Generally, the microfluidic device is configured to detect the presence of the molecular species in a sample and may further quantify the amount of the species therein. The device may use an electrochemical technique, such as a voltammetric or coulometric technique, for such analysis. In some embodiments, the device is an amperometric sensor (i.e., it detects the redox current produced by the oxidation of the molecular species over time at a fixed voltage potential). In some embodiments, the device includes a potentiostat. Another embodiment of the present invention may include electrochemical methods for measuring the amount of a molecular species in a sample, such as amperometry, cyclic voltammetry, fast scan cyclic voltammetry, pulsed voltammetry, step voltammetry, thin-layer electrochemistry, and chronocoulometry.

The electrode assembly may comprise one, two, three or more electrodes. In some embodiments, the electrode assembly comprises one electrode (i.e., a working electrode). In some embodiments, the microfluidic device may comprise a two- or three-electrode configuration. Thus, in some embodiments, the electrode assembly comprises a working electrode and a reference electrode. In some embodiments, the electrode assembly may comprise a working electrode, a reference electrode and a counter electrode. Further, the electrode assembly may comprise at least one integrated electrode having a sensor width 111 and a sensor pitch 112.

The electrode assembly may further include one or more insulating materials or components to physically contain at least a portion of the electrode or electrodes, or to insulate electrodes from one another. In some embodiments, the electrode assembly can comprise a coating to protect the electrode or electrodes from the environment and/or to enhance the biocompatibility of the electrode assembly. For example, the electrode assembly may comprise a biocompatible polymeric coating covering those portions not covered by a gas permeable membrane, so long as such coating does not interfere with the ability of the device to detect the molecular species.

Suitable electrode materials include any electrically conductive metals and other materials such as, but not limited to, platinum, palladium, rhodium, ruthenium, osmium, iridium, tungsten, nickel, copper, gold, silver, and carbon and carbon fibers, as well as, oxides, dioxides, combinations, or alloys thereof. In some embodiments, the electrically conductive material is selected from carbon, including glassy carbon, carbon fibers, platinum, including platinized platinum, tungsten, silver/silver chloride, gold, copper, indium, tin oxide, iridium oxide, nickel, and combinations thereof. In some embodiments, the working electrode comprises a material selected from platinum, platinized platinum, tungsten, gold, carbon, carbon fiber, and combinations thereof. In some embodiments, the reference electrode comprises silver/silver chloride. In some embodiments, the counter electrode comprises platinum.

According to one embodiment, the electrode assembly 100 comprises at least one working electrode 101 that is integrated or otherwise coupled to the body. According to one embodiment, the microfluidic device may have a plurality of electrodes configured to be in electrical communication with a detector, such as a potentiostat, for measuring current at the electrodes.

Further, the microfluidic device includes a gas permeable membrane 120 disposed on at least one of the integrated working electrodes 101. The membrane may comprise a polysiloxane network wherein one or more silicon atoms in the polysiloxane network is covalently attached to an alkyl group and one or more silicon atoms in the polysiloxane network is covalently attached to a fluorinated alkyl group. In some embodiments, the polysiloxane network is a condensation product of a silane mixture comprising an alkylalkoxysilane and a fluorosilane. The chemical structure and the relative amounts of the silanes in the silane mixture can be varied to alter the biocompatibility, surface wettability and porosity characteristics of the polysiloxane network, depending upon the intended use of the device.

In one embodiment, the microfluidic device 10 includes a body, which may be a substantially planar body comprising a substantially planar substrate 20 and a substantially planar cover glass 30. Thus, the substrate 20 and cover glass 30 may be coupled to one another and in one embodiment, may be disposed generally parallel to one another. Thus, the body may have a rectangular cross section when viewed along its longitudinal axis. The substrate 20 may further comprise an integrated reference electrode 103. According to one embodiment, the integrated reference electrode comprises silver/silver chloride. The substrate 20 may further comprise at least one integrated working electrode 101 and at least one integrated counter electrode 102. In another embodiment, the cover glass may comprise a plurality of integrated electrodes, at least one of the plurality of integrated electrodes being an integrated working electrode and at least one of the plurality of integrated electrodes being an integrated counter electrode. The integrated working electrode 101 may be selected from the group consisting of platinum, platinized platinum, tungsten, gold, carbon, carbon fiber and combinations thereof. The integrated counter electrode 102, according to one embodiment, comprises platinum.

Another aspect of the present invention includes one or more microfluidic channels 25 defined within the body, such as a longitudinal channel defined between the substrate 20 and the cover glass 30. The channel 25 is configured to guide or otherwise house a sample in the device. In one embodiment, a channel 25 may be partially defined by an insulating material 40 disposed on the substrate 20. Thus, the substrate 20, cover glass 30, and insulating material 40 may cooperate to define the channel 25. For example, FIG. 1 shows that the insulating material 40 includes a pair of raised tracks disposed on the substrate 20 so as to define the channel 25 therebetween. According to one embodiment, the microfluidic channel 25 may have a channel width (as measured between the insulating material) of about 3 mm and a channel height (as measured between the substrate and the cover glass) of about 40 $\mu$m. Other embodiments of the invention may include a channel having a channel height and width suitable for measuring a gaseous species, such as NO, from the necessary flow of a sample comprising about 100 $\mu$L or less. One skilled in the art will appreciate a number of combinations of channel height, width, and cross sections exist to accomplish the necessary flow of such a sample. For example, the channel may have different cross sections, such as rectangular or a combination of planar and/or curved surfaces, which may depend on the sample to be analyzed.

As previously mentioned, the body of the microfluidic device may comprise a substrate 20 and a cover glass 30. According to one embodiment shown in FIG. 2, the cover glass may define an inlet aperture 26 and an outlet aperture 27, the inlet aperture being configured to accept a sample reservoir. As such, the microfluidic channel 25, the inlet aperture 26, the outlet aperture 27, and the sample reservoir may be configured to be in fluid communication with one another and the integrated electrode assembly. According to one embodiment, the microfluidic channel 25 may comprise a proximal end 28 and a distal end 29, wherein the fluid flow of the microfluidic sample travels from the proximal end to the distal end. Further, the fluid flow of the microfluidic sample may be oriented in a perpendicular fashion to the longitudinal orientation of the plurality of the integrated electrodes. As such, according to one embodiment, the flow of the microfluidic sample traverses each of the integrated working electrode, integrated reference electrode, and integrated counter electrode. The flow of the microfluidic sample may be encouraged by a number of methods known to those skilled in the art. According to one embodiment, the sample may be engaged to flow from the inlet aperture to the outlet aperture by positive pressure applied to the sample at the inlet aperture by a peristaltic pump, a syringe pump, or by gravity. In another embodiment, the flow of the microfluidic sample may be encouraged by applying negative pressure to the outlet aperture.

As previously mentioned, the planar body of the microfluidic device may comprise a substrate 20 and a cover glass 30. In one embodiment of the invention, the substrate and the cover glass are bonded or otherwise coupled to one another. The substrate may further comprise a plurality of integrated electrodes, which are attached to the substrate by methods known in the art, which may include methods such as soldering or photolithography. In one embodiment, a photoresist mask is applied to the substrate that allows one to selectively pattern a glass substrate with the integrated electrodes. The substrate may also comprise materials such as, for example, glass, paper, cellulose, fabric, polymers (e.g., polydimethylsiloxane, polyimide, polystyrene) or other suitable materials known in the art.

In one embodiment, an insulating material 40 is applied to the plurality of integrated electrodes. One such insulating material may be a high contrast, i-line sensitive epoxy-based photoresist, such as KMPR®. As mentioned herein, the insulating material may be applied to the planar substrate to form, in part, the microfluidic channel. Furthermore, the planar cover glass and the planar substrate may be, for example, fusion bonded together with the insulating material. The planar substrate may further comprise a fiducial marker. Likewise, the planar cover glass may also comprise a fiducial marker. Accordingly, the respective fiducials may be used to align the substrate and the cover glass with respect to one another before the substrate and the cover glass are attached or bonded to one another. According to one embodiment, the fiducial may be etched or created on the substrate and the cover glass by a photolithographic process.

According to one aspect of the present invention, the plurality of electrodes are pre-treated or otherwise prepared before the plurality of electrodes are attached to the planar substrate. Specifically, the integrated working electrode may be treated prior to depositing the gas permeable membrane to the integrated working electrode. In one embodiment, the integrated working electrode may be prepared by plasma etching. Other preparation techniques may include chemical cleaning (e.g., acid etching, base etching, or peroxide etching), UV cleaning, ozone cleaning, sonication in liquid etch solutions, surface silanization with materials such as aminopropyltrimethoxysilane or aminopropyltricholorsilane, and/or platinization of the electrode with 3% chloroplatanic acid via cyclic voltammetry.

Another aspect of the present invention includes a gas permeable membrane 120 disposed on at least one of the integrated electrodes. In some embodiments, the membrane is selectively permeable to one or more of nitric oxide and oxygen. Thus, in some embodiments, the presently disclosed devices comprise membranes that are macro- or meso-porous, and allow some molecules to pass into or through the membrane. Other molecules cannot pass through the membrane because of their size or because of electrostatic, hydrophobic, or lipophilic repulsion with the membrane material. In particular, without being bound to any one particular theory, because the presently described polysiloxane network membranes are composed of silanes having non-hydrophilic substituents (i.e., alkyl or fluorinated alkyl groups), in some embodiments, the networks are selectively permeable to neutral molecules (e.g., NO and $O_2$) in comparison with charged species (e.g., nitrite ($NO_2^-$)).

In one embodiment, the gas permeable membrane may comprise a polysiloxane network wherein one or more silicon atoms in the polysiloxane network is covalently attached to an alkyl group and one or more silicon atoms in the polysiloxane network is covalently attached to a fluorinated alkyl group. One such gas permeable membrane may comprise a mixture of about 80% by volume methyltrimethoxysilane and 20% by volume (heptadecafluoro-1,1,2,2-tetrahydrodecyl)trimethoxysilane. Other suitable gas permeable membranes are disclosed in U.S. Patent Pub. No. 2010/0051480, entitled Nitric Oxide Microsensors Via Fluorosilane-based Xerogel Membranes, which is incorporated herein in its entirety by reference.

Once the plurality of electrodes have been prepared, the gas permeable membrane may be deposited on at least one of the plurality of electrodes. In one embodiment, the gas permeable membrane may be deposited on at least one of the plurality of electrodes by spin-coating. Other methods of depositing the gas permeable membrane on the electrode are known in the art and may include methods such as spread/drop casting, dip-coating, flow coating (i.e., a membrane solution flows through the microfluidic channel to deposit a membrane layer inside the channel), spray coating, and electrodeposition. Further, the gas permeable membrane may be deposited on the electrode with or without a photoresist mask, and further may be deposited by a device, which only allows access to certain areas of the planar substrate.

FIG. 16 illustrates another embodiment of the present invention. The microfluidic device may be configured to measure an amount of nitrosothiols and/or nitrites in a sample. As is known in the art, nitrosothiols may be measured indirectly in biological fluids, such as blood or plasma, by inducing cleavage of the S—N bond of the nitrosothiols and then subsequently measuring or detecting the liberated nitric oxide. Such cleavage of the S—N bond may be accomplished by photolysis, such as by using UV or visible light. Further, copper ions may catalyze the homolytic cleavage of nitrosothiols. According to one embodiment of the present invention, the microfluidic device may include a light source 200 configured to induce cleavage of the S—N bond of nitrosothiols. Further, the microfluidic device may include a first working electrode 101 covered with a gas permeable membrane 120 configured to measure an amount of nitric oxide, a second working electrode 105 configured to measure an amount of nitrite, and a third working electrode 106 covered with a gas permeable membrane 120 configured to measure an amount of nitric oxide produced as a result of the cleavage of the S—N bond of nitrosothiols in the sample. Further, the microfluidic device may also include an aperture 28 configured to access the microfluidic channel for introducing copper ions, or other metal ions known in the art, to induce cleavage of the nitrosothiols. Other suitable microfluidic devices for measuring an amount of nitrosothiols and/or nitrates in a sample are disclosed in U.S. Provisional Patent Application No. 61/452,444, entitled Photolytic Cleavage and Detection of S-Nitrosothiols, which is incorporated herein in its entirety by reference, and filed concurrently with the present application.

FIGS. 17a, 17b, and 18 illustrate microfluidic devices according to additional embodiments of the present invention. As shown, the microfluidic device may further comprise a substrate 20 and a cover glass 30 further comprising a plurality of fiducial markers 15. Specifically, the fiducial markers 15 may be used to align the substrate and the cover glass with respect to one another before the substrate and the cover glass are coupled or bonded to one another. According to on embodiment, a fiducial marker may be etched or created on the substrate and the cover glass by a photolithographic process. Further, the cover glass and the substrate may be, for example, fusion bonded together with an insulating material. According to one embodiment, the electrode assembly may comprise an electrode coated with a gas-permeable membrane disposed on a cover glass, and a reference electrode disposed on a substrate. Furthermore, FIG. 18 demonstrates a fabrication process according to one embodiment of the present invention, which may include at least one of applying a mask, exposing a photoresist material, removing the photoresist material to expose the substrate, and etching of the substrate.

As described above, embodiments of the microfluidic device may be used for measuring the amount of a molecular species in a sample. The sample can be a biological sample or an environmental sample. In particular, the presently disclosed sensors can be used to specifically and quantitatively detect a gaseous species that is dissolved in a solution, such as an aqueous solution of biological media, either in vitro or in vivo. Thus, in some embodiments, the device is a biosensor. In some embodiments, the gaseous specie may be oxygen or nitric oxide. In particular embodiments, devices provided by the presently disclosed subject matter can detect nitric oxide.

In some embodiments, the device can detect and quantify nitric oxide or another gaseous species present in a sample at low levels, for example, at levels as low as about 10 nM. In some embodiments, the gaseous species is present at a concentration as low as about 200 pM. For example, the device can selectively measure a gaseous species at concentration levels between about 200 pM and about 50 µM.

Thus, the presently disclosed device may include nitric oxide sensors that can be used as research tools to investigate the biological actions of NO, to monitor medical conditions related to NO-regulated processes, and to monitor the degradation, therapeutic, or adverse actions of a variety of therapeutics, including the actions of NO-releasing therapeutics, such as nitroglycerin or amyl nitrite. NO-releasing therapeutics include those which release NO themselves, as well as those which trigger the release of NO by the body. In some embodiments, the presently disclosed device can be used as neurochemical research or medical diagnostic tools.

In some embodiments, the biological sample in which the gas is being measured is one of a cell, a tissue, an organ, or a biological fluid. Cells can include, for example, heart cells, brain cells, macrophage cells, neutrophil cells, monocyte cells, and endothelial cells. Biological fluids can include blood, plasma, gastric fluid, milk, saliva, cerebrospinal fluid (CSF) and the like. Biological samples can also include cell cultures, tissue cultures and cell or tissue extracts.

In some embodiments, the device can be used to measure NO in the brain or in a brain cell or brain tissue. In some embodiments, the device can be used to measure NO levels in blood, for example, in a blood vessel. In some embodiments, the device can be used to determine an immune response by measuring NO in a macrophage cell, a neutrophil cell, or in tissue comprising or believed to comprise a macrophage and/or neutrophil cell. In some embodiments, the device can be used to measure the NO concentration in a single cell.

In some embodiments, the methods of the presently disclosed subject matter can be useful for measuring the concentration of nitric oxide (or another biologically relevant gaseous species) in a biological sample derived from or present in a subject. In some embodiments, the subject is a human subject, although it is to be understood that the subject can be any living organism, including microbes, plants, and animals. Accordingly, the term "subject" as used herein, refers to any invertebrate or vertebrate species. The methods and devices of the presently disclosed subject matter are particularly useful as diagnostic and research tools for use with samples from warm-blooded vertebrates. Thus, the presently disclosed subject matter concerns mammals and birds. More particularly, herein provided are methods for the study and/or diagnosis of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the study and diagnosis of birds, including those kinds of birds that are endangered, kept in zoos, as well as fowl, and more particularly domesticated fowl, e.g., poultry, such as turkeys, chickens, ducks, geese, guinea fowl, and the like, as they also are of economical importance to humans. Thus, subjects include livestock, including, but not limited to, domesticated swine (pigs and hogs), ruminants, horses, poultry, and the like. Subjects also include animals generally used in biological or medical research, such as rodents (e.g., rats, mice and hamsters) and primates.

In some embodiments, the sample is derived from, but is no longer present in a living subject. Thus, in some embodiments, NO can be measured in a sample ex vivo. In some embodiments, the sample is present in a living subject, and NO concentration can be measured in a sample in vivo. In some embodiments, the sample is an environmental sample, such as an air sample or a water sample taken from, for example, a lake, a river, a stream, a pond, or any other outdoor water source. Thus, for example, the presently disclosed device can be used to measure NO levels in air, produced, for example, as waste from combustion engines or power plants. The device can also be used to quantify levels of dissolved NO or $O_2$ in aquatic environments, to assess the ability of such environments to sustain animal or plant life.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Characterization of Bare Electrodes

Figure 4:
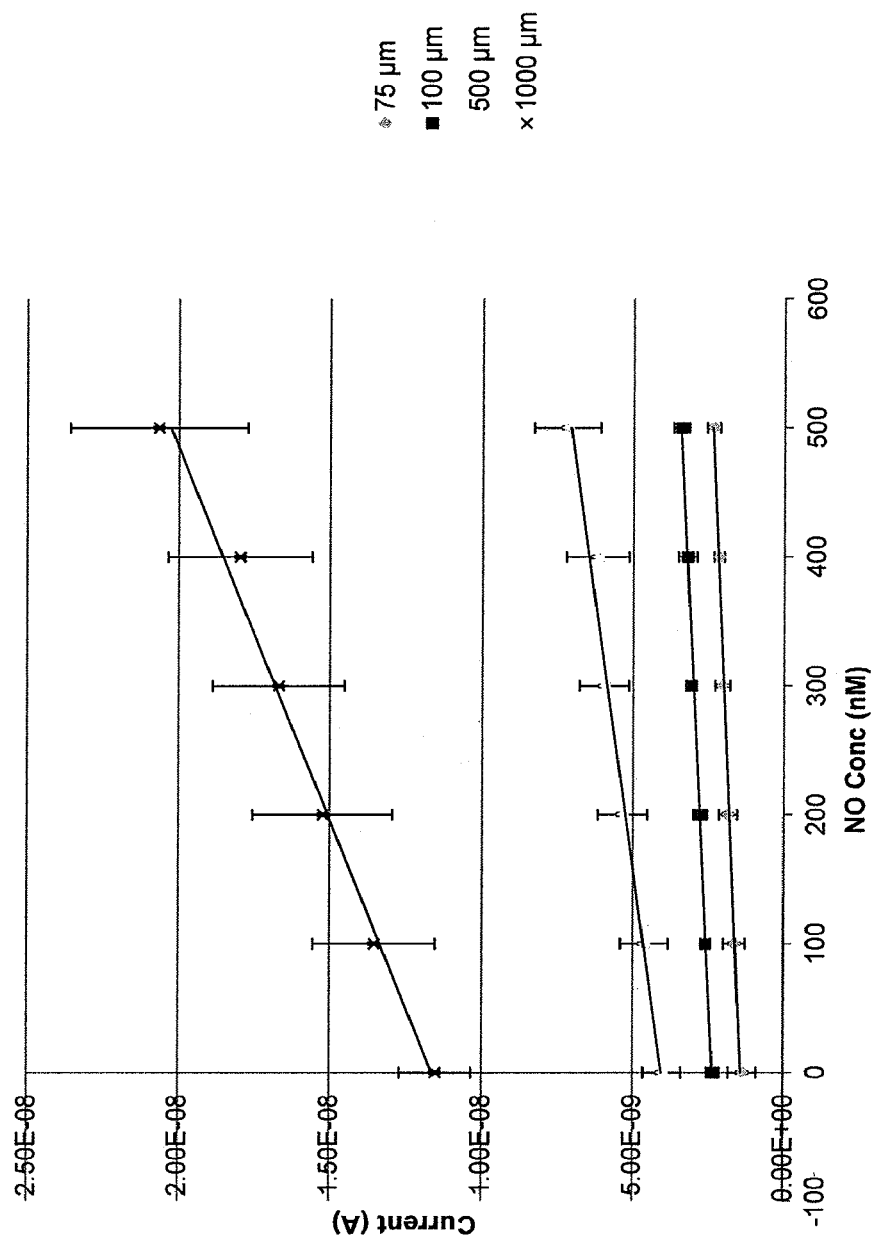
FIG. 4 is a graph showing the calibration curve corresponding to a plurality of bare electrodes having varying sensor widths according to one embodiment of the present invention.
Figure 5:
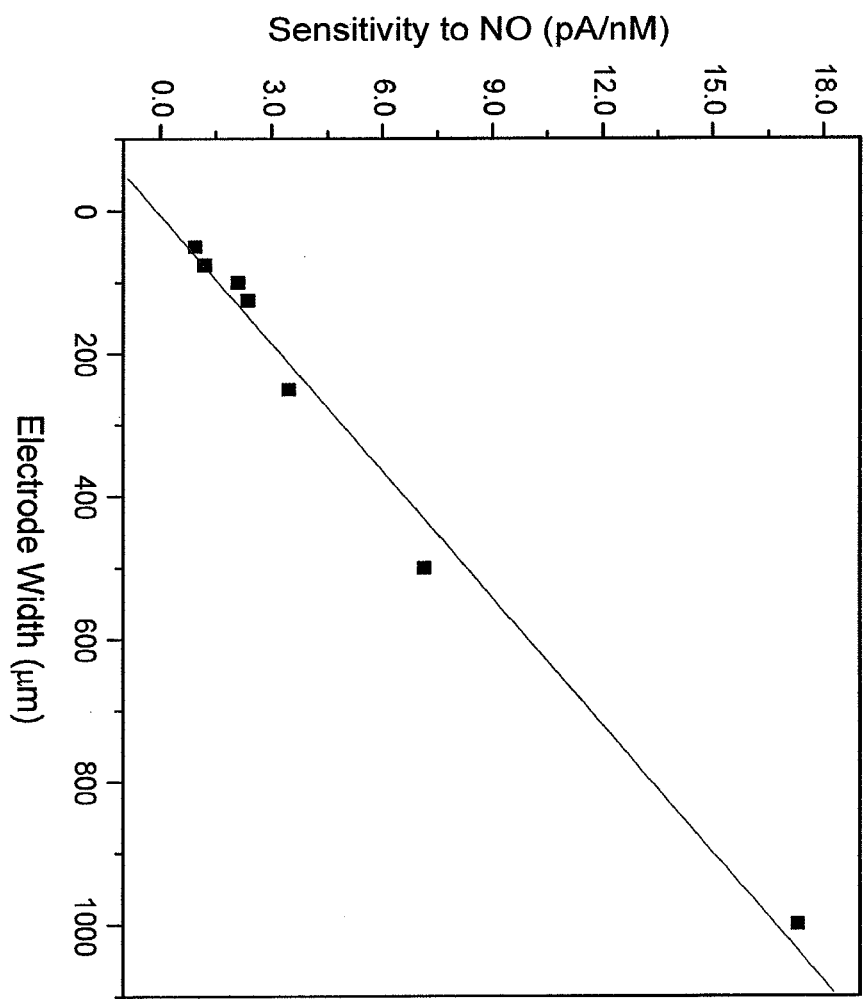
FIG. 5 is a graph illustrating the sensitivity to NO of various electrodes having varying sensor widths according to one embodiment of the present invention.

FIGS. 4 and 5 illustrate the characterization of a plurality of bare platinum electrodes having varying electrode sensor widths, according to exemplary embodiments of the present invention. Specifically, FIG. 4 illustrates the variable responses of bare platinum electrodes having sensor widths between 75 µm to 1000 µm to concentrations of NO between 0 nM and 500 nM. FIG. 5 illustrates the sensitivity of various bare platinum electrodes to NO, the electrodes having sensor widths between 50 µm to 1000 µm. For example, a bare platinum electrode having a sensor width of 75 µm has a sensitivity of about 1.9 pA/nM and a limit of detection of 200 nM. In another example, a bare platinum electrode having a sensor width of 100 µm has a sensitivity of about 2.17 pA/nM and a limit of detection of about 260 nM. In yet another example, a bare platinum electrode having a sensor width of 500 µm has a sensitivity of about 6.07 pA/nM and a limit of detection of about 312 nM. In another example, a bare platinum electrode having a sensor width of 1000 µm has a sensitivity of about 17.3 pA/nM and a limit of detection of about 337 nM.

Example 2

Electrodes Coated with Gas-Permeable Membrane

Figure 6:
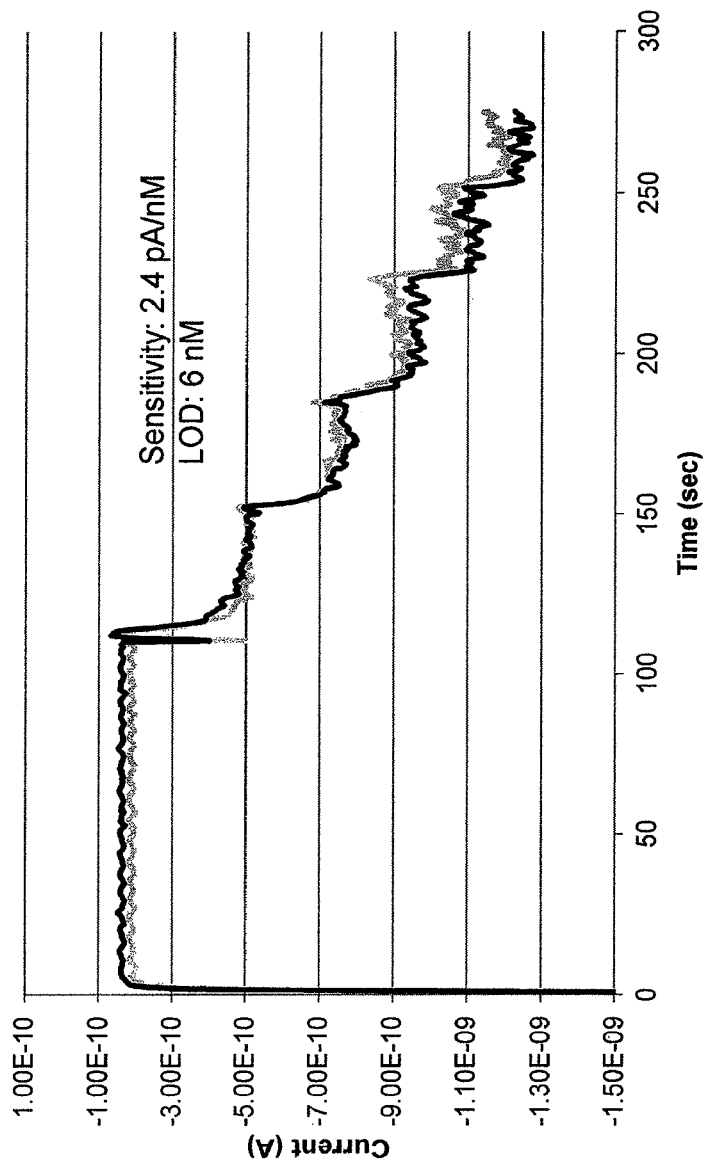
FIG. 6 is a graph of the dynamic response of a platinum electrode having a sensor width of 100 μm, the electrode being covered with a gas permeable membrane according to one embodiment of the present invention.
Figure 7:
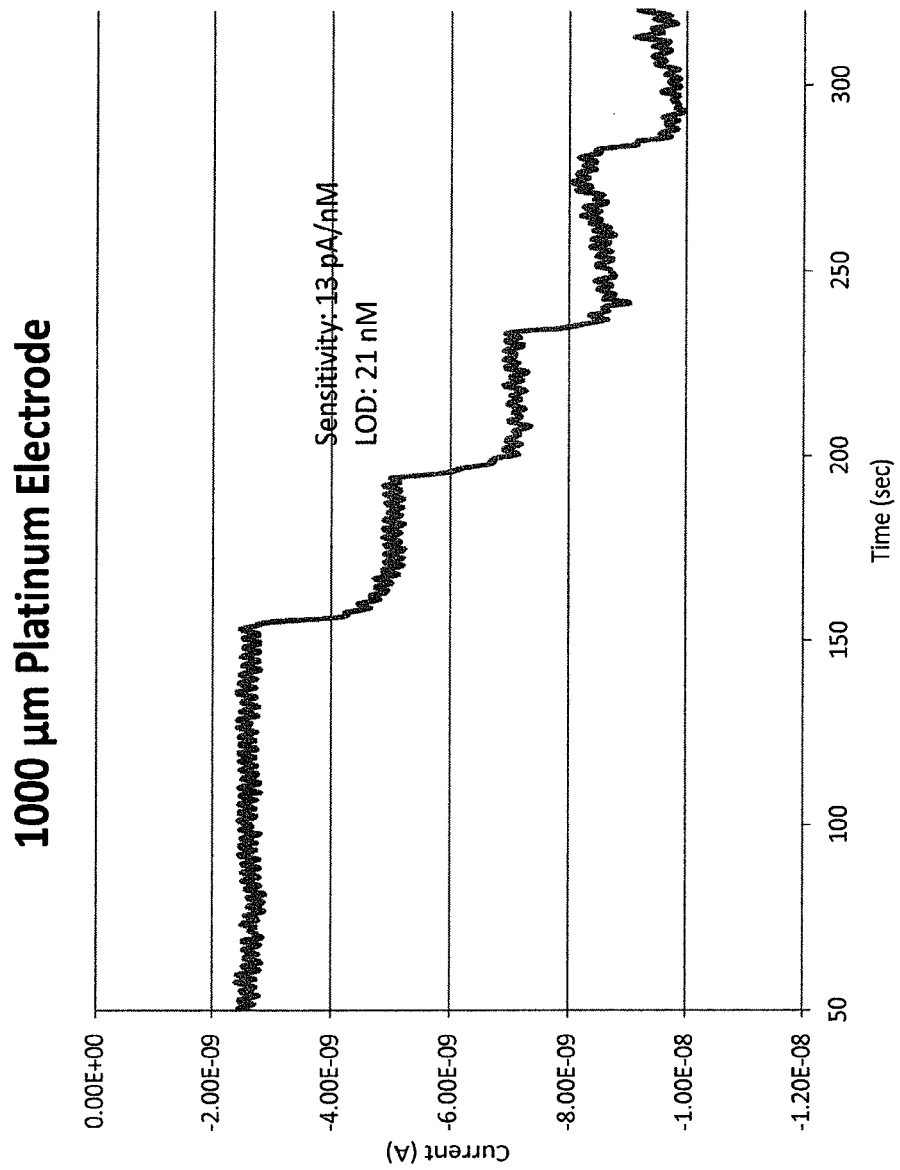
FIG. 7 is a graph of the dynamic response of a platinum electrode having a sensor width of 1000 μm, the electrode being covered with a gas permeable membrane according to one embodiment of the present invention.

FIGS. 6 and 7 illustrate the dynamic response of platinum electrodes coated in a gas permeable membrane to nitric oxide at concentrations of 100 nM, according to embodiments of the present invention. The gas permeable membrane, according to one embodiment, may comprise a mixture of about 80% by volume methyltrimethoxysilane and 20% by volume (heptadecafluoro-1,1,2,2-tetrahydrodecyl)trimethoxysilane. Specifically, FIG. 6 discloses the dynamic response of a platinum electrode coated in such a gas permeable membrane having a sensor width of 100 µm to NO at concentrations of 100 nM. The 100 µm coated-electrode has a sensitivity of about 2.04 pA/nM and a limit of detection of about 6 nM. FIG. 7 illustrates the dynamic response of a platinum electrode coated in such a gas permeable membrane having a sensor width of 1000 μm to NO at concentrations of 100 nM, according to one embodiment. The 1000 μm coated-electrode has a sensitivity of about 13 pA/nM and a limit of detection of about 21 nM.

Figure 8:
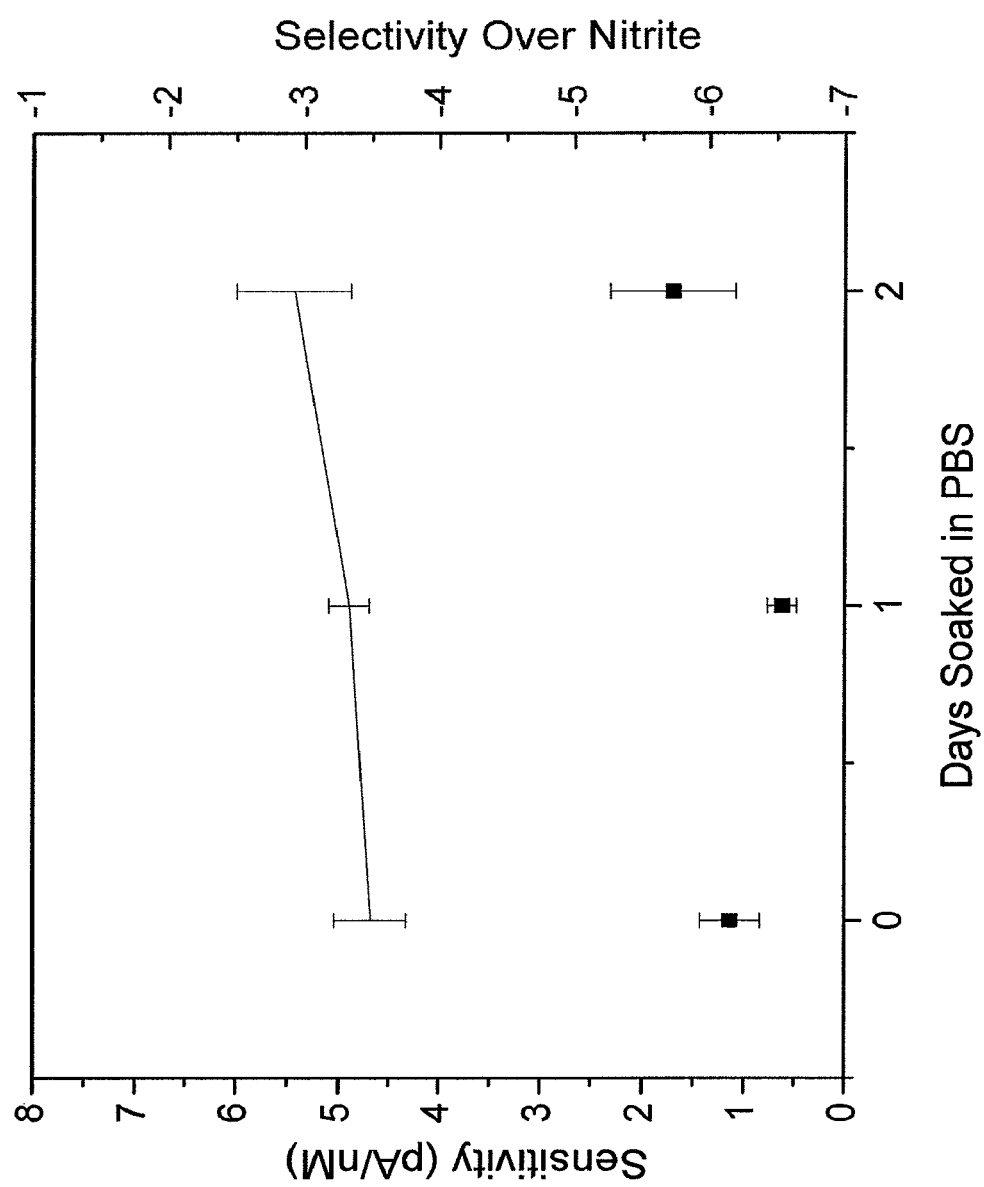
FIG. 8 is a graph illustrating the gas permeable membrane's sensitivity to NO and selectivity over nitrite over a period of time according to one embodiment of the present invention.

According to one embodiment, FIG. 8 illustrates the stability of an electrode coated with a gas permeable membrane, the gas permeable membrane, according to one embodiment, comprising a mixture of about 80% by volume methyltrimethoxysilane and 20% by volume (heptadecafluoro-1,1,2,2-tetrahydrodecyl)trimethoxysilane. Specifically, the graph of FIG. 8 illustrates the selectivity and the sensitivity of coated-electrodes, which are soaked in a phosphate buffered saline solution, over a period of time lasting two days.

Example 3

Response of Gas-Permeable Membrane Coated Electrode to Biological Fluids

Figure 9:
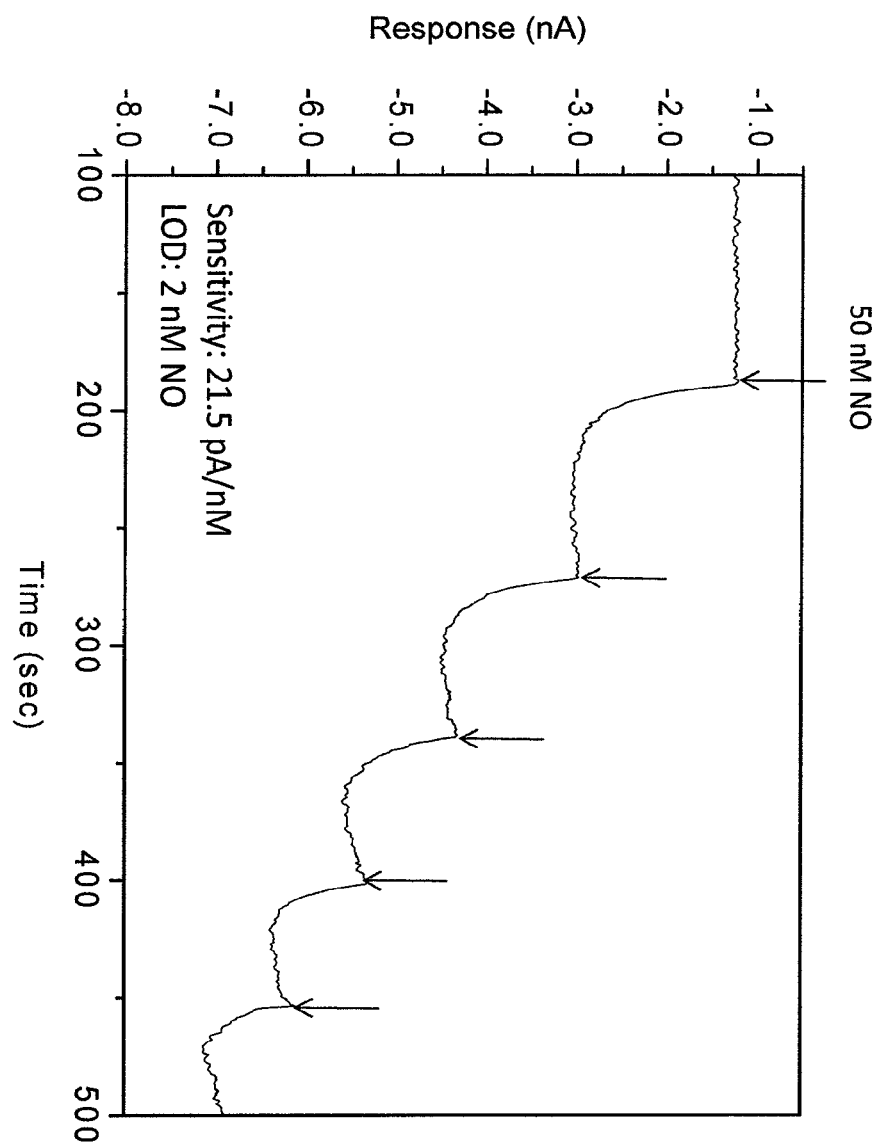
FIG. 9 is a graph of the dynamic response of one embodiment of the microfluidic device to simulated wound fluid, such as 10% fetal bovine serum according to one embodiment of the present invention.
Figure 10:
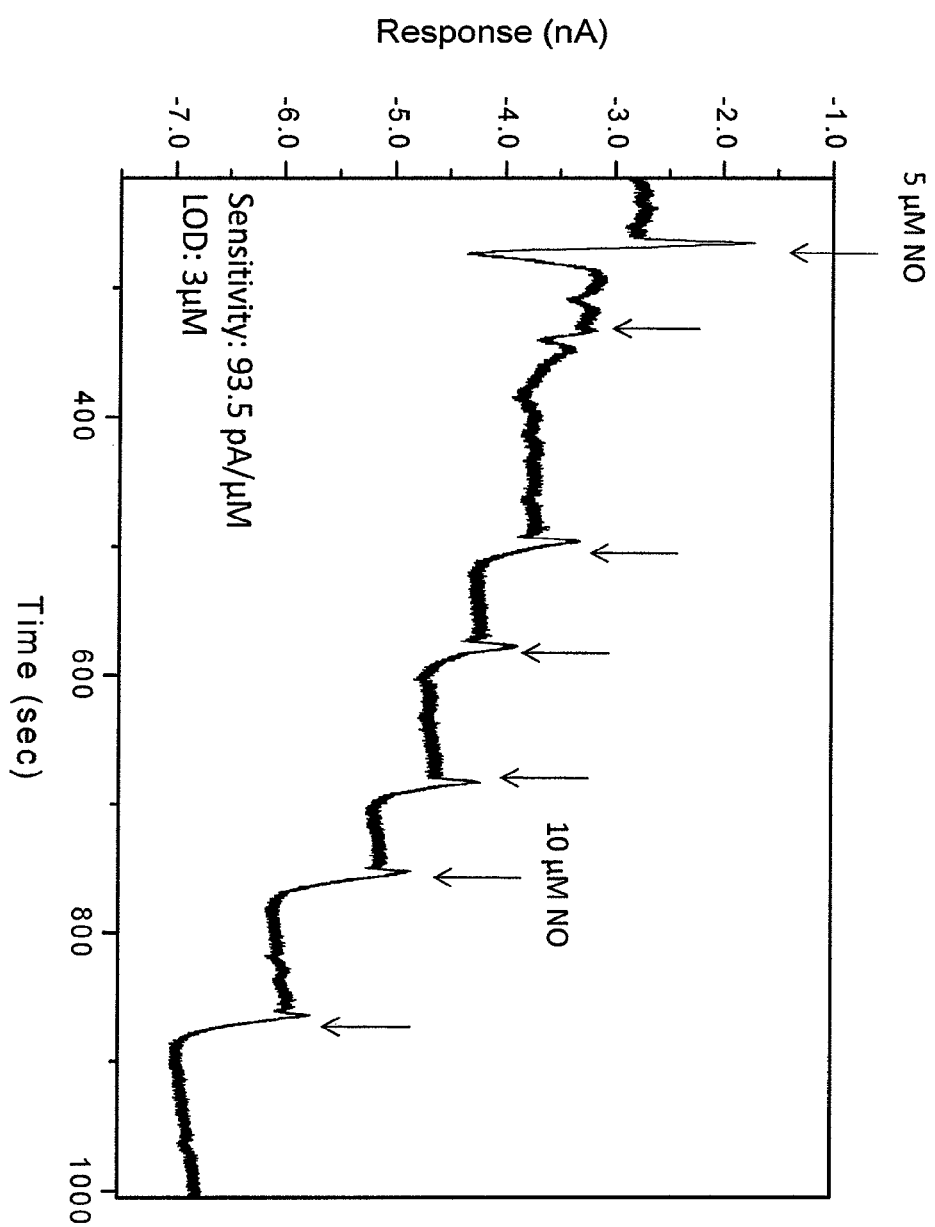
FIG. 10 is a graph of the dynamic response of one embodiment of the microfluidic device to whole blood according to one embodiment of the present invention.

FIGS. 9 and 10 illustrate the dynamic response of the microfluidic device, according to one embodiment, to biological fluids having concentrations of nitric oxide between 50 nM and 10 μM. Specifically, FIG. 9 illustrates the dynamic response of the microfluidic device, according to one embodiment, to simulated wound fluid, such as 10% fetal bovine serum, having a concentration of nitric oxide of about 50 nM. The microfluidic device has a sensitivity of about 21.5 pA/nM in response to the simulated wound fluid. FIG. 10 illustrates the dynamic response of a microfluidic device, according to one embodiment, to whole blood having concentrations of nitric oxide between 5 μM to 10 μM. The microfluidic device has a sensitivity of about 93.5 pA/μM in response to the whole blood.

FIGS. 14 and 15 illustrate the dynamic response and sensitivity of a microfluidic device, according to one embodiment, to biological fluids, such as simulated wound fluid and whole blood. The simulated wound fluid may be 10% fetal bovine serum, and the whole blood may be deoxygenated or oxygenated blood. Specifically, FIG. 14 illustrates the dynamic response and sensitivity of a microfluidic device, according to one embodiment to simulated wound fluid, such as 10% fetal bovine serum, having NO concentrations between 200 nM and 800 nM. The microfluidic device has a sensitivity of about 4.45 pA/nM and a limit of detection of about 1.25 nM in response to the 10% fetal bovine serum having NO concentrations between 200 nM and 800 nM. FIG. 15 illustrates the dynamic response and sensitivity of a microfluidic device, according to one embodiment to whole blood that is deoxygenated and to whole blood that is oxygenated. The whole blood may have concentrations of NO between 5 μM and 20 μM. In response to the deoxygenated blood, the microfluidic device had a sensitivity of about 35 pA/μM and a limit of detection of about 153 nM. In response to the oxygenated blood, the microfluidic device had a sensitivity of about 54 pA/μM and a limit of detection of about 233 nM.

Example 4

Response of Microfluidic Device to Interferents

FIG. 13 illustrates the selectivity of platinum electrodes coated in a gas permeable membrane, according to one embodiment of the present invention. Further, FIG. 13 illustrates the response to interferents such as nitrite, ascorbic acid, and acetaminophen at concentrations of 100 μM. Specifically, FIG. 13 illustrates the response of a platinum electrode having a sensor width of 100 μm and a gas permeable membrane, the gas permeable membrane being applied to the electrode by a spread-cast method. The gas permeable membrane, according to one embodiment, may comprise a mixture of about 80% by volume methyltrimethoxysilane and 20% by volume (heptadecafluoro-1,1,2,2-tetrahydrodecyl)trimethoxysilane. The amperometric selectivity coefficients of the electrodes for NO in the presence of interfering species, such as nitrite, ascorbic acid, and acetaminophen were calculated using the following equation, where $I_{NO}$ and $I_j$ are the measure current values for the target analyte (NO) and interfering species (j=nitrite, ascorbic acid, and acetaminophen).

$$\text{Selectivity} = \log\left(\frac{I_j}{I_{NO}}\right) \quad (1)$$

The selectivity of a platinum electrode having a sensor width of 100 μm and a gas permeable membrane to nitrite was about −4.7, to ascorbic acid was about −3.8, and to acetaminophen was about −3.9.

FIGS. 11 and 12 illustrate embodiments of the dynamic response of electrodes in a microfluidic device to a phosphate buffered saline solution having concentrations of nitric oxide between 100 nM and 800 nM and to a phosphate buffered saline solution having concentrations of nitrite, ascorbic acid, and acetaminophen of about 100 μM. Specifically, FIG. 11 comparatively illustrates the dynamic response of an electrode coated with a gas permeable membrane and a bare platinum electrode. The gas permeable membrane, according to one embodiment, may comprise a mixture of about 80% by volume methyltrimethoxysilane and 20% by volume (heptadecafluoro-1,1,2,2-tetrahydrodecyl)trimethoxysilane. The coated-electrode had a sensitivity of about 2.3 pA/NM of NO and a limit of detection of about 760 pM. The bare platinum electrode had a sensitivity of about 2.7 pA/nM of NO and a limit of detection of about 579 pM.

FIG. 12 illustrates an embodiment of the selectivity of an electrode coated with a gas permeable membrane and a bare platinum electrode to interferents, such as nitrite, ascorbic acid, and acetaminophen, in a phosphate buffered saline solution. The gas permeable membrane, according to one embodiment, may comprise a mixture of about 80% by volume methyltrimethoxysilane and 20% by volume (heptadecafluoro-1,1,2,2-tetrahydrodecyl)trimethoxysilane. The interferents of nitrite, ascorbic acid, and acetaminophen each had a concentration of about 100 μM. The coated-electrode had an amperometric selectivity coefficient less than about −6 for nitrite, about −4.3 for ascorbic acid, and about −3.7 for acetaminophen. The bare platinum electrode had an amperometric selectivity coefficient less than about −5 for nitrite, about −2.3 for ascorbic acid, and about −2.6 for acetaminophen.

Example 5

Exemplary Method of Manufacturing a Microfluidic Device

According to one embodiment of the present invention, a microfluidic device may be configured to measure an amount of a molecular specie in a sample. For example, a microfluidic device, manufactured according to one exemplary method, is illustrated in FIG. 19. The microfluidic device 10 may include a body 11, which may be a substantially planar body comprising a substantially planar substrate 20 and a substantially planar cover glass 30. The substrate 20 and the cover glass 30 may be coupled to one another and in one embodiment, may be disposed generally parallel to one another. The substrate 20 may comprise at least one integrated membrane coated working electrode 101 and at least one integrated bare working electrode 104. Further, the cover glass 30 may include at least one integrated reference electrode 103.

In one embodiment, the microfluidic device may include a plurality of planar platinum electrodes deposited onto a glass substrate. For example, the plurality of platinum electrodes may be patterned onto a glass substrate via photolithography and/or evaporative metal deposition. According to one example embodiment, the glass substrate may include dimensions of 4 inches by 4 inches. Further, the glass substrate may be cleaned with distilled water, isopropanol, and/or nitrogen gas prior to the deposition of the platinum electrodes. In another embodiment, the glass substrate may be dried at approximately 95 degrees Celsius for approximately 5 minutes before the deposition of the platinum electrodes. After the glass substrate cools to room temperature after the drying process, a photoresist may be deposited onto the glass substrate via spincoating at approximately 3000 rpm for approximately 45 seconds. The glass substrate may then be heated to approximately 115 degrees Celsius for approximately 2 minutes.

According to some embodiments, the electrode pattern may be produced by exposure through a mylar mask for approximately 10 seconds using a mask aligner, such as a Karl Suss MA6/BA6 mask aligner equipped with a 350 W UV lamp. Subsequently, the electrode pattern may be developed in an alkaline developer for approximately 1 minute. The glass substrate may then be rinsed with distilled water, dried with nitrogen gas, and/or heated to approximately 115 degrees Celsius for approximately 2 minutes. The glass substrate may also be cleaned with oxygen plasma at 100 W for approximately 1 minute.

The electrodes may then be produced by depositing 10 nm of titanium and 150 nm of platinum via a magnetron sputtering system, such as the Kurt Lesker PVD 75 magnetron sputtering system. Afterwards, the substrate may be soaked in acetone to remove the remaining photoresist and/or excess metal. Accordingly, a glass substrate may include a platinum electrode assembly comprising a plurality of platinum electrodes having a width of approximately 100 μm.

In another embodiment, the electrode assembly on the glass substrate may include a gas permeable membrane. In some embodiments, the glass substrate with the electrode assembly may be rinsed with distilled water, dried with nitrogen, and/or heated to approximately 95 degrees Celsius for approximately 5 minutes. Substrates may then be cleaned with oxygen plasma at 100 W for approximately 1 minute and/or heated at approximately 95 degrees Celsius for approximately 60 minutes. The regions of the glass substrate configured to be coated with a gas permeable membrane may be masked with a photoresist by spin-coating the glass substrate at approximately 500 rpm for approximately 10 seconds and/or at approximately 3000 rpm for approximately 40 seconds. In some embodiments, the electrode pattern may be exposed via a chrome mask for approximately 80 seconds using a mask aligner equipped with a 350 W UV lamp. Subsequently, the glass substrate may be heated to approximately 95 degrees Celsius for approximately 10 minutes. The electrode pattern may then be developed with a mask developer for approximately 6 minutes. The glass substrate may then be rinsed with isopropanol, dried with nitrogen gas, and/or heated to approximately 115 degrees Celsius for approximately 10 minutes.

According to some embodiments, the glass substrate may also include an adhesion layer deposited via three injections of approximately 5 mL at 130 degrees Celsius. The gas permeable membrane may include a mixture of methyltrimethoxysilane and a fluorinated trimethoxysilane. According to one embodiment, 600 μL absolute ethanol, 120 μL MTMOS, 30 μL 17FTMS, 160 μL distilled water, and 10 μL 0.5 M HCl may be added sequentially to a 1.5 mL tube. Each addition of a material to the tub may be followed by a vigorous mixing of the tube. Once the final material is added, the tube may be placed in a centrifuge for approximately 60 minutes. In one embodiment, the solution may be pipetted across the electrode assembly and spread-cast across the electrodes with the pipette tip continuously for approximately 60 seconds to ensure an even coating of the solution. The glass substrate may then be cured for approximately 12 hours to ensure proper curing. Afterwards, the remaining photoresist may be removed by soaking the glass substrate in distilled water for approximately 60 minutes.

According to one embodiment, the microfluidic device may include at least one reference electrode fabricated on a separate glass microscope slide. The glass microscope slide may be cleaned with oxygen plasma at approximately 100 W for approximately 5 minutes. Additionally, the glass microscope slide may be masked with tape such that one-third of the slide from each end is masked leaving the middle third exposed. The reference electrodes may be produced by depositing approximately a 10 nm chromium adhesion layer followed by a 1.0 μm silver layer via a magnetron sputtering system. Additionally and/or alternatively, approximately ¼ inch strips of double-sided Kapton® polyimide tape may be placed parallel to one another along the longitudinal axis of the glass slide at opposite lateral ends of the slide, thus forming a channel along the longitudinal axis of the glass slide. The glass slide including at least one reference electrode and the glass substrate including at least one working electrode may be coupled by clamping the slide and the substrate to one another and then heating the components to approximately 100 degrees Celsius for approximately 5 minutes. Additionally and/or alternatively, the ends of the channel may be sealed and then a pair of 8 mm diameter inlet/outlet reservoirs may be affixed to the microfluidic device using a high-strength, chemical-resistant epoxy. Subsequently, electrical wires may be soldered directly to the solder-on pads of each electrode to provide for an electrical connection. Further, the reference electrodes may be formed via chemical oxidation of the silver electrodes by exposing the silver electrodes to approximately 50 mM of iron chloride for approximately 10 seconds and then subsequently rinsing the silver electrodes with distilled water.

Example 6

Response of Microfluidic Device

FIGS. 20-23 illustrate the dynamic response of the microfluidic device, according to one embodiment of the present invention. Specifically, FIG. 20 illustrates the dynamic response of a gas-permeable membrane coated electrode compared to a bare electrode in response to NO in a phosphate-buffered solution flowing at approximately 15 μL/min. The dynamic response of the bare electrode is illustrated as the dotted line, while the dynamic response of the gas-permeable membrane coated electrode is characterized by the solid line. The response to the NO for the bare electrode was approximately 2.0 pA nM$^{-1}$ NO, while the response to the NO for the gas-permeable membrane coated electrode was approximately 1.4 pA nM$^{-1}$ NO. The gas-permeable membrane coated electrode exhibited a slightly lower sensitivity compared to the bare electrode due to the slow NO diffusion across the gas-permeable membrane to the electrode surface. The limit of detection for the bare electrode and the gas-permeable membrane coated electrode was approximately 880 and 840 pM NO respectively.

FIG. 21 illustrates the dynamic response of the microfluidic device in response to interfering species such as nitrite, ascorbic acid, acetaminophen, and uric acid at concentrations of 100 µM. The selectivity of the bare and membrane coated electrodes was about −5.3 to nitrite, about −4.2 to ascorbic acid, about −4.0 to acetaminophen, and about −5.0 to uric acid respectively. The dynamic response to the interfering species of the bare electrode is characterized by the dotted line, while the dynamic response of the membrane-coated electrode is characterized by the solid line.

FIG. 22 illustrates the dynamic response of the microfluidic device to 1 µM increases of NO concentrations in whole blood. The addition of a saturated NO solution to the whole blood was easily detectable and produced a current proportional to the amount of NO added to the whole blood. Accordingly, a limit of detection for the microfluidic device was approximately 472 nM NO. As such, a limit of detection of approximately 500 nM would be less than that required for NO analysis in blood for a number of disease states, where the NO concentration has been known to be in the µM range.

FIG. 23 illustrates the dynamic response of the microfluidic device to simulated wound fluid, such as a 10% Fetal Bovine Serum in water. The microfluidic device manufactured according to an exemplary method of manufacturing a microfluidic device responded to NO additions (e.g., 200 nM increase) in a simulated wound fluid sample having a limit of detection of approximately 18 nM. The improved limit of detection for the example microfluidic device to NO in a simulated wound fluid compared to whole blood may be attributed to the lack of scavenging elements in the simulated wound fluid that may be present in the whole blood, such as blood proteins and hemoglobin.

Example 7

Response of Microfluidic Device in Detecting Sepsis

FIG. 24 illustrates the dynamic response of a microfluidic device in a number of porcine models, according one exemplary embodiment of the present invention. Specifically, FIG. 24 illustrates the temporal percentage change in NO levels in porcine models that have been exposed to cecal ligation and perforation, which provides for a model of sepsis that depicts infection and the immune response in severe sepsis. Accordingly, a microfluidic device according to embodiments of the present invention may be configured to detect an elevation of blood NO levels during the onset of sepsis. Further, in some embodiments, the microfluidic device may be configured to detect the elevation of NO levels prior to the manifestation of clinical signs and symptoms of sepsis, which may allow for earlier intervention and supportive care. As shown in FIG. 24, the percentage change in the amount of NO increases over time in those porcine models that have been exposed to cecal ligation and perforation. Although not illustrated in FIG. 24, these increases in NO levels preceded changes in cardiac output, respiratory rates, and/or blood lactate levels. Further, control porcine models showed no dramatic rise in NO levels, but rather the NO levels decreased as the animals recovered from surgeries.

Accordingly, embodiments of the present invention may provide advantages and improvements over the prior art for measuring an amount of a molecular species in a sample. One such advantage may include measuring, in real-time, an amount of molecular species in smaller sample sizes. Embodiments of the present invention include a microfluidic device for measuring an amount of molecular species in a smaller sample without the additional need to stir, homogenize or otherwise prepare the sample. Further, another advantage aspect of embodiments of the present invention includes obtaining a smaller sample than was previously necessary to measure an amount of molecular species. As such, a microfluidic device according to one embodiment may measure a molecular specie from smaller amounts of biological fluids, such as blood, plasma, and urine.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not limited to the specific embodiments disclosed and that modifications and other embodiments are intended to be included within the scope of the appended claims. Although specific terms are employed herein, they are used in a generic and descriptive sense only and not for purposes of limitation.

We claim:

1. A micro fluidic device for measuring an amount of a molecular species in a sample, the device comprising:
    a substantially planar body;
    an electrode assembly comprising at least one electrode coupled to the body;
    a gas permeable membrane disposed on and coating the at least one electrode; and a detector for measuring current at each of the electrodes
    wherein said electrode is pre-treated prior to coating the electrode with the gas permeable membrane so as to increase adhesion of the gas permeable membrane to the electrode.

2. The device according to claim 1, wherein the molecular species is selected from the group consisting of nitric oxide, nitrite and s-nitrosothiols.

3. The device according to claim 1, wherein the sample comprises a volume of about 1 to 100 µl.

4. The device according to claim 1, wherein the substantially planar body further comprises a planar substrate and a planar cover glass coupled to the substrate.

5. The device according to claim 4, wherein the substantially planar body further comprises a channel comprising a proximal end and a distal end, wherein the channel is defined between the planar substrate and the planar cover glass and is configured to receive at least a portion of the sample therein:
    and, wherein the substantially planar body optionally further comprises:
    an inlet aperture defined in the planar cover glass and configured to be in fluid communication with the channel; and
    an outlet aperture defined in the planar cover glass and configured to be in fluid communication with the channel.

6. The device according to claim 5, wherein the substantially planar body further comprises an insulating material cooperating with the planar substrate and the planar cover glass to define the channel.

7. The device according to claim 4, wherein the planar cover glass and/or the planar substrate comprises a plurality of integrated electrodes wherein the plurality of integrated electrodes optionally comprises one or more of
an integrated working electrode;
an integrated counter electrode; or
an integrated reference electrode.

8. The device according to claim 4, wherein the planar substrate comprises a material selected from the group consisting of glass, polydimethylsiloxane, polyimide, polystyrene, paper, cellulose, and fabric.

9. The device according to claim 7, wherein the device comprises one or more of
a) an integrated working electrode that is selected from the group consisting of platinum, platinized platinum, tungsten, gold, carbon, carbon fiber, and combinations thereof and
b) the integrated counter electrode comprises one or more of platinum or silver/silver chloride.

10. The device according to claim 7, wherein at least one of the plurality of integrated electrodes further comprises:
a sensor width; and
a sensor pitch.

11. The device according to claim 10, wherein the sensor width is about 50 to 1000 µm and/or the sensor pitch is about 50 to 2500 µm.

12. The device according to claim 5, wherein the channel comprises:
a channel width of about 0.5 to 5 mm; and
a channel height of about 20 to 100 µm.

13. The device according to claim 1, wherein the gas permeable membrane comprises a polysiloxane network wherein one or more silicon atoms in the polysiloxane network is covalently attached to an alkyl group and one or more silicon atoms in the polysiloxane network is covalently attached to a fluorinated alkyl group.

14. The device according to claim 13, wherein the gas permeable membrane comprises a member selected from the group consisting of
a) a mixture comprising fluorosilane in a range of about 1% to 50% by volume; and
b) a mixture of about 80% by volume methyltrimethoxysilane and 20% by volume (heptadecafluoro-1,1,2,2-tetrahydrodecyl)trimethoxysilane.

15. A method of making a microfluidic device for measuring an amount of a molecular specie in a sample, the method comprising:
attaching a plurality of electrodes to a substantially planar body;
depositing a gas permeable membrane on at least one of the plurality of electrodes; and
coupling a detector for measuring current to at least one of the plurality of electrodes, wherein the plurality of electrodes comprises at least one of
an integrated working electrode;
an integrated reference electrode; or
an integrated counter electrode
and pre-treating the electrode prior to coating the electrode with a gas permeable membrane to increase adhesion of the gas permeable membrane to the electrode.

16. The method according to claim 15, wherein the gas permeable membrane comprises a polysiloxane network wherein one or more silicon atoms in the polysiloxane network is covalently attached to an alkyl group and one or more silicon atoms in the polysiloxane network is covalently attached to a fluorinated alkyl group.

17. A method according to claim 16, wherein the gas permeable membrane comprises a mixture of about 80% by volume methyltrimethoxysilane and 20% by volume (heptadecafluoro-1,1,2,2-tetrahydrodecyl)trimethoxysilane.

18. A method according to claim 15, further comprising coupling a substrate to a cover glass so as to define a channel for receiving at least a portion of the sample therein.

19. A method according to claim 18, further comprising applying an insulating material to the substrate such that the substrate, cover glass, and insulating material cooperate to define the channel.

20. A method according to claim 15, further comprising applying a photoresist material to the body.

21. A microfluidic device for measuring an amount of a molecular species in a sample, the device comprising a member selected from the group consisting of:
a) a body comprising a substrate and a cover glass coupled to one another, wherein a channel is defined between the substrate and the cover glass for receiving at least a portion of the sample therein;
an electrode assembly comprising at least one electrode coupled to the body;
a gas permeable membrane disposed on and coating the at least one electrode; and
a detector for measuring current at each of the electrodes so as to determine the amount of a molecular species in the sample wherein said electrode is pre-treated prior to coating the electrode with the as permeable membrane so as to increase adhesion of the gas permeable membrane to the electrode; and
b) a body comprising a channel for receiving a sample having a volume of less than about 400 µL therein;
an electrode assembly comprising at least one electrode coupled to the body;
a gas permeable membrane disposed on and coating the at least one electrode; and
a detector for measuring current at each of the electrodes so as to determine the amount of a molecular species in the sample wherein said electrode is pre-treated prior to coating the electrode with the gas permeable membrane so as to increase adhesion of the gas permeable membrane to the electrode.

* * * * *